(12) United States Patent
Giuseppin et al.

(10) Patent No.: US 8,465,911 B2
(45) Date of Patent: Jun. 18, 2013

(54) NATIVE POTATO PROTEIN ISOLATES

(75) Inventors: Marco Luigi Federico Giuseppin, Gieten (NL); Catrinus Van Der Sluis, Veendam (NL); Marc Christiaan Laus, Groningen (NL)

(73) Assignee: Cooperatie AVEBE U.A., Veendam (NL)

( * ) Notice: Subject to any disclaimer, the term of this patent is extended or adjusted under 35 U.S.C. 154(b) by 788 days.

(21) Appl. No.: 12/513,971

(22) PCT Filed: Oct. 25, 2007

(86) PCT No.: PCT/NL2007/050513
§ 371 (c)(1),
(2), (4) Date: Aug. 25, 2009

(87) PCT Pub. No.: WO2008/069650
PCT Pub. Date: Jun. 12, 2008

(65) Prior Publication Data
US 2010/0040591 A1 Feb. 18, 2010

(30) Foreign Application Priority Data
Nov. 10, 2006 (EP) ..................................... 06077000

(51) Int. Cl.
*C12Q 1/00* (2006.01)
(52) U.S. Cl.
USPC ............................................ 435/4; 435/7.71
(58) Field of Classification Search
USPC ................................................... 435/4, 7.71
See application file for complete search history.

(56) References Cited

FOREIGN PATENT DOCUMENTS

| EP | 1264545 A1 | 12/2002 |
|---|---|---|
| WO | 9742834 A1 | 11/1997 |
| WO | 9959623 | 11/1999 |
| WO | 2004082397 A1 | 9/2004 |

OTHER PUBLICATIONS de Jongh "Globular proteins" Progress in Biotechnology, 2003, 23:31-86.*
Alt et al. "Optimization of glycoalkaloid analysis for use in inductrail potato fruit juice downstreaming", Eng. Life Sci., 2005, 5(6):562-567.*
Baker et al. "Development of a pilot-plant process for the preparation of a trypsin inhibitor-rich fraction from potatoes", Ind. Eng. Chem. Prod. Res. Dev., 1982, 21:80-82.*
Koningsveld et al., "Effects of pH and Heat Treatments on the Structure and Solubility of Potato Proteins in Different Preparations", Journal of Agricultural and Food Chemistry, vol. 49, pp. 4889-4897; 2001.
Ralet et al., "Fractionation of Potato Proteins: Solubility, Thermal Coagulation and Emulsifying Properties", Lebensmittel Wissenschaft Und Technologie, Academic Press, vol. 33, No. 5, pp. 380-387; 2000.
Pouvreau et al., "Relative Abundance and Inhibitory Distribution of Protease Inhibitors in Potato Juice from cv. Elkana", Journal of Agricultural and Food Chemistry, vol. 49, pp. 2864-2874; 2001.
Broek et al., "Structural Characterization of Potato Protease Inhibitor I (Cv. Bintje) after Expression in *Pichia pastoris*", Journal of Agricultural and Food Chemistry, vol. 52, pp. 4928-4934; 2004.
Straetkvern et al., "Expanded Bed Absorption for Recovery of Patatin from Crude Potato Juice", Kluwer Academic Publishers, vol. 7, pp. 333-345; 1999.
Yun Bai, Charles E. Glatz, Bioprocess Consierations for Expanded-Bed Chromatography of Crude Canola Extract: Sample Preparation and Adsorbent Reuse, Biotechnology and Bioengineering, vol. 81, No. 7, Mar. 30, 2003, pp. 775-782, © 2003 Wiley Periodicals, Inc.
Mustafa A. Mustafa, et al., A Software Tool to Assist Business-Process Decision-Making in the Biopharmaceutical Industry, The Advanced Centre for Biochemical Engineering, University College London, Biotechnol. Prog. 2004, vol. 20, No. 4, pp. 1096-1102, © 2004 Amer. Chemical Society and American Inst. of Chem. Engineers Published on Web May 7, 2004.
Ping Li, et al, Expanded Bed Adsorption/Desorption of Proteins with Streamline Direct CST I Adsorbent, Dept. of Chem. Engineering, Univ. of Porto, Rua Dr, Roberto Fries, published online Mar. 29, 2006 in Wiley InterScience (www.interscience.wiley.com) © 2003 Wiley Periodicals, Inc.

* cited by examiner

*Primary Examiner* — Susan Hanley
*Assistant Examiner* — Bin Shen
(74) *Attorney, Agent, or Firm* — Hoffmann & Baron, LLP

(57) ABSTRACT

The invention relates to a process for native potato protein isolation, to native potato protein isolates, to the use thereof, and to a food product comprising a native potato protein isolate. The invention provides a novel isolation process for obtaining highly pure native potato protein isolates having a glycoalkaloid concentration of less than 150 ppm.

14 Claims, 8 Drawing Sheets

NATIVE POTATO PROTEIN ISOLATES

This application is the U.S. National Phase of, and Applicants claim priority from, International Application Number PCT/NL2007/050513 filed 25 Oct. 2007 and European Patent Application No. 06077000.5 filed 10 Nov. 2006, each of which are incorporated herein by reference.

BACKGROUND OF THE INVENTION

The invention relates to a process for native potato protein isolation, to native potato protein isolates, to the use thereof, and to a food, nutraceutical and pharmaceutical product comprising a native potato protein isolate.

The undiluted juice from potato tuber is called potato fruit juice. Potato fruit juice may be produced by washing and rasping potatoes and separating the starch and fibres by various techniques, such as centrisieves, hydrocyclones and decanters. Fresh potato fruit juice is a complex mixture of soluble and insoluble material comprising proteins, starch, minerals, toxic glycoalkaloids and monomeric and polymeric reactive phenols.

Fresh potato fruit juice is however not very stable. Oxidation leads to conversion of phenolic compounds into quinones which rapidly combine into a dark polymer residue. During the oxidation process reaction the potato proteins can partially cross-link, which dramatically reduces the solubility of the proteins. The complexity and instability of the potato fruit juice makes the separation and isolation of minimally denatured or modified proteins a complicated and economically demanding process.

Native potato proteins can tentatively be divided into three classes (i) the patatin family, highly homologous acidic 43 kDa glycoproteins (40-50 wt. % of the potato proteins), (ii) basic 5-25 kDa protease inhibitors (30-40 wt. % of the potato proteins) and (iii) other proteins mostly high molecular weight proteins (10-20 wt. % of the potato proteins) (Pots et al., *J. Sci. Food. Agric.* 1999, 79, 1557-1564). Potato protein is rich in lysine and may form an excellent supplement for lysine-poor proteins such as those of cereal. The nutritional value of total potato protein have been shown to be greater than that of casein and comparable to that of whole egg white protein.

Patatin is a family of glycoproteins that have lipid acyl hydrolase and transferase activities and accounts for up to 40 wt. % of the total soluble protein in potato tubers.

Protease inhibitors can be divided into different groups based on their molecular weight. The different groups of protease inhibitors are identified as protease inhibitor I (molecular weight of about 39 kDa), carboxypeptidase inhibitor (molecular weight of about 4 100 Da), protease inhibitors IIa and IIb (molecular weight of about 20.7 kDa), and protease inhibitor A5 (molecular weight of about 26 kDa). The ratio of these different groups of protease inhibitors in the total potato protein depends on the potato variety. Protease inhibitors from potato have a broad range of potentially important applications. Protease inhibitors have for instance shown to be useful in the treatment of diabetes, for eliciting satiety in mammals, for reducing the risk of skin cancer, for inhibiting the growth of bacteria, and for preventing or treating inflammation on pruritis of skin and intestine, see for instance WO-A-99/059623.

Despite its unique nutritional qualities, potato protein is currently only used as animal feed, because the available products exhibit a number of serious drawbacks.

One of the major drawbacks is that the recovery of potato protein from the effluent of potato starch mills is typically carried out on an industrial scale by heat coagulation. During the heat coagulation process, the potato proteins become heavily denatured and as a consequence lose functional properties that are required for applications in the food, nutraceutical and pharmaceutical industry, such as solubility in water.

Other, milder methods for recovering potato proteins, such as membrane filtration applied directly to potato fruit juice and precipitation methods show a low purity and a lack of selectivity and are unable to separate functionalities, see for instance WO-A-97/42834.

There is a commercial interest in a process for producing native total potato protein isolate, native patatin isolate and native protease inhibitor isolate. The term "native potato protein" is used in this application is meant to refer to the potato protein without any significant physical or (bio)chemical modification or inactivation, in particular denaturation. Existing methods for isolating potato proteins and potato protein fractions include fractionation, ion exchange, gel permeation, ultrafiltration, affinity and mixed-mode chromatography and fractionation by heat coagulation. A disadvantage of these prior art isolation methods is that they lack a strict pH control to maintain good potato protein characteristics. Furthermore, they do not sufficiently deal with undesirable contaminants. In particular, glycoalkaloid contaminants are not sufficiently removed.

Glycoalkaloids are well-known anti-nutritional factors. The glycosylated forms (such as α-solanine and α-chaconine) show the highest toxicity. The aglycons (such as solanidine), have a more than 100 fold lower liver toxicity. α-Solanine, α-chaconine and derivatives constitute for more than 95% of the glycoalkaloids in the potato. Other glycoalkaloids include for example tomatine, tomatidenol and demissidine.

Glycoalkaloids have a bitter taste and negatively affect many of the physical and/or biological properties of the proteins, especially when the pH is increased by adhering to the soluble proteins as shown in this application. For food applications the taste threshold is about 140-170 mg of glycoalkaloids expressed as α-solanine per kg product. This threshold strongly limits the applications of prior art native potato protein isolates in foods.

The present inventors have found that the poor solubility of glycoalkaloids such as α-solanine at pH values typically above 6.2 results in an excessive adherence of glycoalkaloids and other compounds, such as polyphenols, to the potato proteins.

Partial removal of glycoalkaloids has been achieved by various ultrafiltration methods at excessive diafiltration conditions, see for instance WO-A-97/42834. The HPLC method employed (Friedman M. et al., J. Agric. Food Chem. 2003, 51, 2964-2973 or Houben et al., *J. Chromatogr. A* 1994, 661, 169-174) does not detect the aglycons that are formed by enzymatic hydrolysis after prolonged processing of potato fruit juice as described. Ultrafiltration can remove some glycoalkaloids and salts, but does not remove high molecular contaminants, such as polyphenols and proanthocyanidines and coloured derivatives thereof, such as epicatechins and anthocyanines, that are formed at pH values below 4.5.

Glycoalkaloids can also be removed by enzymatic hydrolysis. However, this does not lead to removal of aglycon, which also binds to the potato proteins with negative effects on their physical and/or biological properties. Therefore, both a HPLC method (Friedman M. et al., J. Agric. Food Chem. 2003, 51, 2964-2973) and a colorimetric method (Walls et al., *J. Chem. Ecol.* 2005, 31, 2263-2288) must be used to measure the main glycoalkaloids, the total glycoalkaloids and the aglycons, respectively.

Glycoalkaloid removal by fermentation is not considered relevant for safe native protein production. Conversion by fermentation causes severe technical issues to implement this process at a commercial scale. The bioconversions are costly and have a low productivity. The micro-organisms employed and hygiene are limitations for the application of the derived products for foods.

Other undesirable contaminants in the native potato protein isolate are for instance pectins, proanthocyanidines and fatty acids. Pectins typically lead to flocculation of the isolate at pH values below 5.0.

Sufficiently pure native potato protein fractions of patatin and protease inhibitor cannot be obtained by partial heat coagulation.

Contaminants, such as polyphenols, in the patatin fraction lead to very variable physical properties in terms of colour and solubility at various pH. The presence of protease inhibitor and other contaminants with a surface active function in the patatin fraction has a negative effect on the good emulsifying and gelling properties of patatin. Also, further purification of the patatin fraction improves the foaming and emulsification properties, as well as the foaming and emulsion stability of patatin.

On the other hand, a protease inhibitor fraction containing patatin contaminants is less useful in e.g. pharmaceutical applications.

Accordingly, there remains a need for an efficient process for isolating native potato protein and native potato protein fractions that have a high degree of purity.

SUMMARY OF THE INVENTION

Object of the invention is to provide a process that allows for an excellent isolation of native total potato protein and native potato protein patatin and protease inhibitor fractions in pure form.

A further object of the invention is to provide native potato protein isolates that have a high solubility at various pH values and are essentially free from undesired contaminants.

One or more of these objectives are met by the invention, which provides an isolation process for native potato proteins. Accordingly, the invention is directed to a process for obtaining a native potato protein isolate comprising patatin and protease inhibitor, comprising the steps of subjecting potato fruit juice to a flocculation by a divalent metal cation at a pH of 7-9;

centrifuging the flocculated potato fruit juice, thereby forming a supernatant;

subjecting the supernatant to expanded bed adsorption chromatography operated at a pH of less than 11, and a temperature of 5-35° C. using an adsorbent capable of binding potato protein, thereby adsorbing the native potato protein to the adsorbent; and eluting at least one native potato protein isolate from the adsorbent with an eluent.

DETAILED DESCRIPTION OF THE INVENTION

The process according to the invention leads to a highly pure native potato protein isolate with a minimum of denatured protein and stable solubility.

According to the invention, the potato fruit juice is pre-treated with a divalent metal cation at a pH of 7-9, preferably 7.0-7.5, to flocculate undesired material, followed by a separation of the flocks by centrifugation. A particularly suitable divalent metal cation is $Ca^{2+}$. It has been found that this pre-treatment removes undesired material such as negatively charged polymers, pectins, glycoalkaloids, and micro-organisms from the potato fruit juice. In particular, the removal of pectins and glycoalkaloids is advantageous, since these compounds adhere to the potato proteins and may cause flocculation. These compounds thus lead to an unstable protein isolate in terms of solubility and other physical properties.

In the second step of the process, the supernatant is subjected to expanded bed adsorption chromatography. This technique is described in WO-A-2004/082397, which document is hereby incorporated by reference. In contrast to the method described in WO-A-2004/082397, according to process of the invention it is advantageous to keep the temperature of the starting material below 35° C. for a better stability of patatin. Furthermore, in the process of the invention it is preferred to use a moderately high flow rate, typically in the range of 600-1 200 cm/h.

The expanded bed adsorption chromatography is operated at a pH of less than 11, preferably at a pH of less than 10.

The native potato proteins in the pre-treated potato fruit juice are isolated from the supernatant by binding them onto a suitable adsorbent in the expanded bed adsorption column.

Column materials that bind native potato proteins include mixed-mode adsorbentia such as Amersham Streamline™ Direct CST I (GE Healthcare), Fastline adsorbentia (Upfront Chromatography A/S), macroporous adsorbentia such as Amberlite™ XAD7HP (Röhm & Haas Company) and ion exchange adsorbents (for patatin isolates and purification see G. Koningsveld, "*Physico-chemical and functional properties of potato proteins*", PhD thesis, Wageningen University, Wageningen, The Netherlands, 2001; for protease inhibitor isolates see L. Pouvreau, "*Occurrence and physico-chemical properties of protease inhibitors from potato tuber (Solanum tuberosum)*", PhD thesis, Wageningen University, Wageningen, The Netherlands, 2004). The adsorbent with adsorbed native potato proteins is subsequently eluted with a suitable eluent in order to retrieve the native potato protein isolate. The eluent preferably has a pH in the range of 4-12, more preferably in the range of 5.5-11.0.

Preferably, the native potato protein isolate has an isoelectric point above 4.8, a molecular weight of more than 4 kDa and a glycoalkaloid concentration of less than 150 ppm.

In a preferred embodiment using mixed-mode adsorbentia the proteins can be fractionated to both isoelectric point and molecular weight. This allows to separate the patatin and protease inhibitor fractions. Patatin isolates are eluted at a pH of 5.7-8.7, preferably at a pH of 5.8-6.2. Protease inhibitors are eluted at a pH of 5.8-12.0, preferably at a pH of 6.0-9.5.

The mixed-mode adsorbentia can be used in two modes. The first mode is selective elution, which comes down to binding of essentially all of the potato protein and subsequently eluting a first desired potato protein fraction with an appropriate buffer and eluting a second desired potato protein fraction with another appropriate buffer. The second mode is selective adsorption, which comes down to binding of a first desired potato protein fraction on one column at an elevated pH, and adjusting the effluent to a lower pH so that a second desired potato protein fraction can bind on a second column.

Selective elution is described in the examples. Selective adsorption for instance involves passing a potato fruit juice at pH 5.0-7.0, typically at pH 6.0, over a first column to bind the protease inhibitor fraction. The protease inhibitor fraction may be eluted using an appropriate buffer as described above. The effluent of the first column is adjusted to a pH of 4.5-5.0, preferably to a pH of 4.8, and passed over a second column to bind the patatin fraction. Patatin is eluted using an appropriate buffer as described above. Selective adsorption yields a robust processing and higher purity of the isolates than selective elution.

After elution, the native potato proteins may advantageously be concentrated by ultrafiltration. This may further reduce the amount of remaining glycoalkaloids. The choice of the ultrafiltration membrane material can strongly influence the selectivity. Preferably, the ultrafiltration membrane is negatively charged and comprises regenerated cellulose, polyethersulphones and polysulphones (PES). Protease inhibitors isolates may be concentrated using PES based membranes with a molecular cut-off of 2-20 kDa, and to some extent 30 kDa. Patatin isolates may be concentrated using PES based membranes with a molecular cut-off of 5-30 kDa or a regenerated cellulose based membrane with a molecular cut-off of 5-30 kDa. These membranes can be implemented as tubular, spiral wound, hollow fibre, plate and frame, or as cross-rotational induced shear filter units.

Ultrafiltration membranes should be operated at conditions to both concentrate and remove glycoalkaloids effectively. In the presence of high glycoalkaloid levels the pH values should be below pH 6.2. At a pH higher than 6.2 glycoalkaloids, such as $\alpha$-solanine, have a very low solubility and will co-concentrate with the proteins. Patatin isolates are ultrafiltrated at pH values of 4.0-6.2, preferably pH 4.5-5.4. For protease inhibitor isolates pH values of 3-7, preferably 3.2-4.5 are used. After removal of glycoalkaloids the pH can be increased to pH 7-10 to enable high fluxes through the membranes. Protease inhibitors are preferably processed at low pH of 3.0-5.0.

The native potato protein isolate thus obtained only contains low levels of, and is preferably essentially free from, toxic components and colour. The isolate is further organoleptically neutral and stable.

Additional purification steps in the process of the invention can be the following. An ion-exchange step may be applied to isolate protease inhibitors or patatin with an alkaline or acid elution. Residual glycoalkaloids and taste and colour may be removed using ion-exchange, polymer adsorbents (such as Amberlite™ and Polyclar®) and mineral adsorbents (such as zeolites, activated carbon and bleach earth).

Apart from the ultrafiltration concentration, the native potato protein isolates obtained by the process of the invention may be concentrated up to more than 20% dry matter by evaporation, freeze concentration, or isoelectric precipitation using carbondioxide. The dry matter of these concentrates can contain more than 85% of protein, preferably more than 90% of protein, based on the nitrogen level (Kjeldahl nitrogen content times 6.25). The dried products can contain more than 90%, preferably more than 92% of protein, with a moisture level of 4-9%.

The invention is further directed to a process in which a native potato protein protease inhibitor isolate is processed into at least one isolate selected from the group consisting of a protease inhibitor I isolate, a carboxypeptidase inhibitor isolate, a protease inhibitor IIa and IIb isolate, and a protease inhibitor A5 isolate. This processing can involve ion exchange or gel permeation chromatography.

The patatin isolate is a preferred source of various valuable enzymes, such as lipase, alkaline phosphorylase (U.S. Pat. No. 0,290,952), apyrase, peroxidase, lipoxygenase, and polyphenol oxidase. Therefore, the patatin isolate has a wide range of applications in food, fine chemical and pharmaceutical industry.

In a further aspect, the invention is directed at the native potato protein isolate obtainable by the process according to the invention. This native potato protein isolate includes the total native potato protein isolate, the native potato protein patatin isolate, and the native potato protein protease inhibitor isolate. These potato protein isolates are characterised by their high degree of purity and stability. The total native potato protein isolate of the invention can have an isoelectric point above 4.8, a molecular weight of more than 4 kDa, and a glycoalkaloid concentration of less than 150 ppm. The isolate is preferably essentially free of organic acids and amino acids.

The native potato protein patatin isolate of the invention can have an isoelectric point of below 5.8, preferably 4.8-5.5, a molecular weight of more than 30 kDa, preferably more than 35 kDa, and a glycoalkaloid concentration of less than 150 ppm.

The native potato protein protease inhibitor isolate of the invention can have an isoelectric point above 5.5, preferably above 5.8, a molecular weight of below 35 kDa, preferably 4-30 kDa, and a glycoalkaloid concentration of less than 150 ppm. A protease inhibitor isolate according to the invention has, on a molecular weight basis, been found to have properties very similar to whey protein. However, it as a considerably higher iso-electric point, which allows a wider pH range in many applications.

Dry native potato proteins can be obtained by spray drying, flash drying or freeze drying. The patatin isolate and total protein isolate are set at a suitable pH to ensure good water solubility. The pH of the concentrates is set to 7.0-9.0, preferably to 7.0-8.0. Concentrates of protease inhibitors can be spray dried using both low pH (3.0-4.0) as well as high pH values (7.0-9.0). The native potato proteins thus obtained have a water solubility of more than 90%, preferably more than 95% at a pH of 7.0 and a temperature of 25° C. Solubility is expressed as the percentage of protein in the supernatant after centrifugation of the solution.

In a preferred embodiment, the native potato protein isolate as obtained after ultrafiltration concentration has a protein content of more than 75% of the dry matter content. The protein content herein is defined as Kjeldahl nitrogen content times 6.25. Preferably the protein content in the native potato protein isolate is more than 80%, more preferably more than 90%, and even more preferably more than 95%.

The inventors further found that the invention allows to obtain a native potato protein isolate with a low sulphite content of less than 10 ppm. Such native potato protein isolate can be safely used in foods, in contrast to the potato protein isolate of WO-A-97/42834 to which large amounts of sulphite are added during ultrafiltration.

The native potato protein isolates of the invention may be characterised by a two-dimensional gel electrophoresis analysis combined with an identification of the key proteins in the isolate using MALDI-TOF mass spectrometry analysis. The proteins can be separated in the two-dimensional gel electrophoresis using a pH gradient from 3 to 8 and a molecular weight of 5-100 kDa.

In another aspect, the invention is directed to the use of a native potato protein patatin isolate as a gelling agent, an emulsifier or foaming agent in a food product. It was found that the gelling, emulsifying and foaming properties of the patatin fraction of the native potato protein isolate according to the invention are enhanced due to the high purity of the isolate.

The invention also relates to the use of a native potato protein patatin isolate as a source of pharmaceutical and therapeutic enzymes.

The invention is further directed to a food product comprising a native potato protein isolate according to the invention. Typical food products include for instance dairy products, ice cream, bakery products, meringues. The nutritional value of the potato proteins is very high and comparable to hen egg protein. This is based on amino acid composition and the experience of these proteins as feed proteins. Its high nutritional value combined with the absence of anti-nutritional glycoalkaloid compounds makes the native potato protein product a very suitable ingredient for infant foods, sports drinks and derived protein hydrolysates.

The invention is also directed to a personal care product comprising a native potato protein isolate according to the invention, such as a skin care cream.

Further, the native potato protein isolates of the invention may be advantageously used in the following applications.

Total Potato Protein Isolates

Total potato protein isolates may be used in vegetarian meat analogues to bind fatty ingredients and/or water.

Total protein isolates show a high waterbinding capacity in various food applications.

Total potato protein isolates may be used in protein hydrolysates using acid hydrolysis or enzymatic hydrolysis, preferably after heat denaturation.

Protease Inhibitor Isolates

It has been found that protease inhibitors show a remarkable foaming capacity which is 5-10 times stronger than patatin isolates. Therefore protease inhibitor isolates may be useful in foamed foods but also in fire extinguishing foam applications.

Protease inhibitor isolates may be used in shaving foam with skin care, e.g. as moisturiser and for their ability to inhibit proteases that cause skin irritation.

Protease inhibitor isolates may be used in diet and clinical foods related to the gastro-intestinal effects of excess pancreatic or microbial activity.

Protease inhibitor isolates can be used to control protein degradation in various foods in particular fermented foods.

Protease inhibitor isolates, particularly in heat inactivated form, have a profound impact on satiety in many food applications and can therefore be used in dietary or slimming products in the prevention or treatment of obesitas, such as diet soft drinks.

The effectiveness of therapeutic enzymes in the gastro-intestinal tract is enhanced when the therapeutic enzymes are blended with protease inhibitors.

Protease inhibitor isolates with high protein solubility and high nutritional value and low off flavour may be used in high protein (sport) drinks. Most of the trypsin inhibitor activity is inactivated by the heat treatment during product manufacturing.

Protease inhibitors may be used to reduce bacterial growth on fresh food such as fish.

Protease inhibitors can be used to inhibit micro-organisms (bacteria) that cause skin problems such as acne and sweat malodour.

Protease inhibitor isolates combined with various charged hydrocolloids, such as pectins can be used as an efficient encapsulating or coacervating agent for fats, oils and volatile flavours.

Patatin Isolates

Patatin isolates may be used in applications with high fat and/or high sugar compositions, such as coffee creamer, spreads (fresh cheese analogues, pâté and the like) or ice cream, e.g. for encapsulating fat. The high emulsifying ability will allow the use of lower amounts of emulsifiers in these compositions at relatively low dosages compared with other commercial protein isolates such as caseinates.

Patatin isolates may be used as stabilizing agents in foams, such as in meringues, whipped cream, coffee creamer, cappuccino foam, foamed creams, aerated deserts, mousse, and the like. In these applications patatin isolates show a high effectiveness. Functionalities such as foaming and structuring can often be obtained with dosages as low as half those wherein caseinates are typically employed.

Patatin isolates may be used for fat emulsions in dressings and mayonnaise (sauce hollandaise), or foamed emulsions such as foamed creams.

Patatin isolates may be used in sausages (knak or frankfurter sausages), e.g. as fat binding agents or water binding agents. Patatin isolates may be used at lower dosages compared with caseinates. In general to ½ to ¼ Of the typical dosages of caseinates can be used without significant adverse effects on gel strength, water binding properties and/or fat binding properties. Due to their excellent emulsifying properties, patatin isolates give small fat droplets resulting in an enhanced flavour release and taste impression in fat based processed meat.

Patatin isolates may be used to enhance viscosity and shelf life of various fermented food products such as yoghurt. It can replace use of whey protein isolates and/or caseinates in desserts and yoghurt recipes.

Patatin isolates, in particular combined with charged hydrocolloids especially carrageenan or alginate, can be used as an efficient and high capacity encapsulating or coacervating agent for fats, oils and volatile flavours.

Patatin isolates show a remarkable combination of properties and can be used as an emulsifier and a gelling protein at the same time. After making a starting emulsion with fats, even after pasteurisation the emulsion can be whipped to foam, or gelled to form a paste or aerated/heated to form a foamed gel.

Protein hydrolysates of native patatin isolates using enzymatic hydrolysis and/or acid hydrolysis.

EXAMPLES

Determination of Foaming Properties

The sample is dissolved in water at pH 5.0, with 30% castor sugar and 125 mM NaCl. The foaming potential or overrun is calculated as:

$$Overrun = \frac{V_{increase}}{V_{initial}}$$

The foam stability is calculate by measuring the volume after 15 and 30 minutes according to the following formula.

$$Foam\ stability = \frac{V_{foam\ at\ t=15'}}{V_{foam\ at\ t=30'}} \times 100\%$$

The foam capacity FC is defined by the following equation.

$$Foam\ capacity = \frac{(foam + remaining\ solution\ (mL))}{starting\ volume\ (mL) \times protein\ concentration\ (g/100\ mL)}$$

Determination of Emulsifying Properties

The sample is dissolved at the desired pH and an emulsion is prepared with a blender (Ultra Turrax) at 10 000 rpm.

1. Samples are diluted 1/125 in demi water and the absorbance is measured at 500 nm in a 1 cm cuvette at least duplicate. This value is defined as the emulsion activity (EA).
2. Samples are taken after 1, 15 and 30 minutes. The emulsion stability, ES, is defined according to the following formula.

$$Emulsion\ stability = \frac{A_{500\ nm\ at\ t=15'}}{A_{500\ nm\ at\ t=30'}} \times 100\%$$

Determination of Gel Strength

The gel strength is determined using a Texture Analyser (TA-HDi Texture Analyser, Stable Micro Systems) with a P75 probe in 40 ml vials.

The protein samples are dissolved for 2 hours with a magnetic stirrer in a 40 ml sample flask at 20° C. The parameters of the texture analyser were set as follows: pre-test speed: 1.00 mm/s, test speed: 0.10 mm/s, post test speed: 2.00 mm/s, distance: 25.0 mm, load cell: 5 kg.

For example the gel strength of an 8% patatin solution heated at 20-90° C. was carried out under the following texture analyser conditions plate: TUK 180-MP31, γ=0.01, f=3 Hz, gap width=1.5 mm Heating in 70 minutes from 20° C. to 90° C., maintain 90° C. for 30 minutes, cooling in 70 minutes from 90° C. to 20° C.

The G' and G" during the heating and gellation of a patatin isolate are given below.

|       | 70 minutes Pa | 170 minutes Pa |
|-------|---------------|----------------|
| G'    | 2 500         | 6 320          |
| G"    | 155           | 1 260          |
| tan α | 0.07          | 0.20           |

Preparation of Native Potato Protein Isolates

Method 1 Patatin Purification Using EBA with Amersham STREAMLINE® Direct CST I Adsorbent.

Figure 1A:
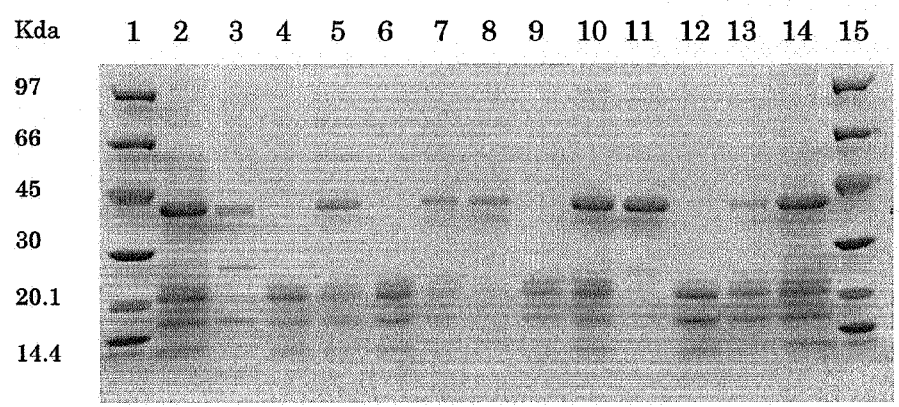
FIG. 1A: One dimensional SDS-PAGE comparison of various potato protein isolates
Figure 1B:
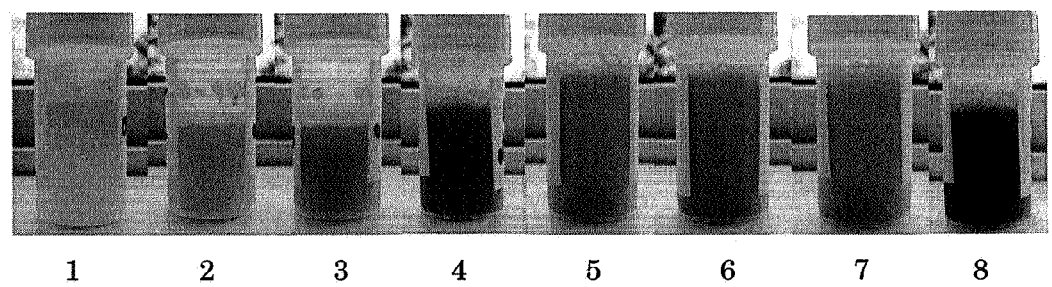
FIG. 1B: Photos of concentrated potato protein fractions

130 ml of STREAMLINE® Direct CST-I column material (25 cm bed height) was equilibrated with 5 column volumes (CV) of 20 mM citrate buffer pH 4.8. Approximately 650 ml (5 CV) of potato fruit juice from the potato factory at Ter Apelkanaal (The Netherlands) was adjusted to a pH of 4.8 and loaded on the column. After loading, the column was washed with 5 CV of 20 mM citrate buffer pH 4.8. Patatin was eluted in 6 CV 20 mM citrate buffer pH 6.0. The eluate was loaded on an SDS-PAGE gel (FIG. 1A lane 3). After elution the patatin fractions (pH 6.1) was concentrated by ultrafiltration using a 30 kDa membrane filter (FIG. 1B sample 1). Method 2 Protease Inhibitor Purification Using EBA with Amersham STREAMLINE® Direct CST I adsorbent.

130 ml of STREAMLINE® Direct CST-I column material (25 cm bed height) was equilibrated with 5 column volumes (CV) of 20 mM citrate buffer pH 6.0. Approximately 650 ml (5 CV) of potato fruit juice from the potato factory at Ter Apelkanaal (The Netherlands) was adjusted to a pH of 6.0 and loaded on the column. After loading, the column was washed with 5 CV of 20 mM citrate buffer pH 6.0. PI was eluted in 3 CV 50 mM NaOH. The eluate was loaded on an SDS-PAGE gel (FIG. 1A lane 4). After elution the protease inhibitor fractions (pH 3.2) were concentrated by ultrafiltration using a 10 kDa membrane filter (FIG. 1B sample 2). Method 3 Total Protein Content Purification Using EBA with Amersham STREAMLINE® Direct CST I Adsorbent.

130 ml of STREAMLINE® Direct CST-I column material (25 cm bed height) was equilibrated with 5 column volumes (CV) of 20 mM citrate buffer pH 4.8. Approximately 650 ml (5 CV) of potato fruit juice from the potato factory at Ter Apelkanaal (The Netherlands) was adjusted to a pH of 4.8 and loaded on the column. After loading, the column was washed with 5 CV of 20 mM citrate buffer pH 4.8. Total protein was eluted in 6 CV 50 mM NaOH and concentrated by ultrafiltration using a 10 kDa membrane. The eluates were loaded on an SDS-PAGE gel (FIG. 1A lane 5 and FIG. 1B sample 3). Method 4 Total Protein Content Purification Using AMBERLITE® XAD7HP Column Material.

160 ml of AMBERLITE® XAD7HP column material (30 cm bed height) was equilibrated with 5 CV of 20 mM citrate buffer pH 5.1. 800 ml of potato fruit juice, adjusted to pH 5.1, was loaded on the column. After loading, the column was washed with 5 CV of 20 mM citrate buffer pH 5.1. Both patatin and protease inhibitor were eluted simultaneously using 50 mM NaOH. The eluate was loaded on an SDS-PAGE gel (FIG. 1A lane 6). After elution the eluate (pH 6.5) was concentrated by ultrafiltration using a 10 kDa membrane filter (FIG. 1B sample 4).

Method 5 Total Protein Content Purification Using Heat Coagulation.

500 ml of potato fruit juice from the potato factory at Ter Apelkanaal (The Netherlands) was heated in a water bath at 87.5° C. for 30 min. The precipitated protein fraction was filtered using a Büchner funnel. Thereafter, the precipitate was washed with water and filtered again. The procedure was performed three times. Finally the patatin precipitate was dried. The patatin precipitate was dissolved in water and loaded on an SDS-PAGE gel (FIG. 1A lane 7). After dissolving the precipitate in water, a suspension formed (FIG. 1B sample 5).

Method 6 Patatin Purification Using Acid Coagulation.

1 000 ml of potato fruit juice from the potato factory at Ter Apelkanaal (The Netherlands) was adjusted to pH 3.0 using 1 M HCl. After standing for 60 min at room temperature, the solution was centrifuged at 5 000 rpm (at 1 076 g) for 20 min. The precipitate was resuspended in water and centrifuged again. This procedure was repeated three times. Finally the precipitate was dried. The precipitate was dissolved in water and loaded on an SDS-PAGE gel (FIG. 1A lane 8 and FIG. 1B sample 6).

Method 7 PI Purification Using Acid/Heat Coagulation.

1 000 ml of potato fruit juice from the potato factory at Ter Apelkanaal (The Netherlands) was adjusted to pH 3.0 using 1 M HCl. After standing for 60 min at room temperature, the solution was centrifuged at 5 000 rpm (at 1 076 g) for 20 min. The supernatant was brought on pH 5.5 using 1 M NaOH. Thereafter, the supernatant was heated in a water bath at 87.5° C. for 30 min. Then, the precipitate was washed and filtered using a Büchner funnel. The procedure was performed three times. Finally, the protease inhibitor precipitate was dried. The protease inhibitor precipitate was dissolved in water and loaded on an SDS-PAGE gel (FIG. 1A lane 9). After dissolving the precipitate in water, a suspension formed (FIG. 1B sample 7).

Method 8 Total Protein Content Purification Using Ultrafiltration.

According to WO 97/42834. To 2 000 ml of potato fruit juice from the potato factory at Ter Apelkanaal (The Netherlands) 0.3% (w/v) $CaCl_2.2H_2O$ and 0.18% (w/v) $Na_2HPO_4.2H_2O$ were added. The mixture was stirred for 5 min at room temperature. The pH was raised to 7.5 using 1 M NaOH. The potato fruit juice was centrifuged at 5 000 rpm for 20 min. The supernatant was concentrated about ten times by ultracentrifugation using a 10 kDa filter. The concentrate was stored at −20° C. The concentrate was loaded on an SDS-PAGE gel (FIG. 1A lane 10). The concentrate appeared as a dark brown solution (FIG. 1B sample 8).

Method 9 Patatin Purification Using EBA with Fastline PRO.

130 ml of Fastline PRO column material (25 cm bed height) was equilibrated with 5 column volumes (CV) of 20 mM citrate buffer pH 4.8. Approximately 650 ml (5 CV) of potato fruit juice from the potato factory at Ter Apelkanaal (The Netherlands) was adjusted to a pH of 4.8 and loaded on the column. After loading, the column was washed with 5 CV of 20 mM citrate buffer pH 4.8. Patatin was eluted in 6 CV of 20 mM citrate buffer pH 6.0. The eluate was loaded on an SDS-PAGE gel (FIG. 1A lane 11). After elution the patatin fractions (pH 6.3) was concentrated by ultrafiltration using a 30 kDa membrane.

Method 10 Protease Inhibitor Purification Using EBA with Fastline PRO.

130 ml of Fastline PRO column material (25 cm bed height) was equilibrated with 5 column volumes (CV) of 20 mM citrate buffer pH 6.0. Approximately 650 ml (5 CV) of potato fruit juice from the potato factory at Ter Apelkanaal (The Netherlands) was adjusted to pH 6.0 and loaded on the column. After loading, the column was washed with 5 CV of 20 mM citrate buffer pH 6.0. PI was eluted in 3 CV of 50 mM NaOH. The eluate was loaded on an SDS-PAGE gel (FIG. A1 lane 12). After elution the protease inhibitor fraction (pH 3.2) was concentrated by ultrafiltration using a 10 kDa membrane.

Method 11 Total Protein Content Purification using EBA with Fastline PRO.

130 ml of Fastline PRO column material (25 cm bed height) was equilibrated with 5 column volumes (CV) of 20 mM citrate buffer pH 4.8. Approximately 650 ml (5 CV) of potato fruit juice from the potato factory at Ter Apelkanaal (The Netherlands) was adjusted to pH 4.8 and loaded on the column. After loading, the column was washed with 5 CV of 20 mM citrate buffer pH 4.8.

Total protein was eluted in 6 CV of 50 mM NaOH and concentrated by ultrafiltration using a 10 kDa membrane. The eluate was loaded on an SDS-PAGE gel (FIG. 1A lane 13).

Example 1

Comparison of the Basic Properties of Native Potato Protein Isolates Using Various Methods

| | Method | | | | | | | | | | |
|---|---|---|---|---|---|---|---|---|---|---|---|
| | 1 Amersham patatin[1] | 2 Amersham PI[2] | 3 Amersham total[3] | 4 Amberlite total[4] | 5 Heat coag. total[5] | 6 Acid coag. patatin[6] | 7 Acid coag. PI[7] | 8 UF total[8] | 9 Fastline Patatin[9] | 10 Fastline PI[10] | 11 Fastline Total[11] |
| Solubility of spray dried product[a] | +/− | + | +/− | +/− | − | − | − | +/− | +/− | + | +/− |
| Solubility stability[b] | + | + | +/− | − | +/− | − | − | − | + | + | +/− |
| Solubility at pH 5-7[c] | + | + | + | + | −− | − | − | +/− | + | + | + |
| Color of the solution[d] | yellow grey | yellow grey | brown grey | brown | grey | grey | grey | dark brown | Yellow grey | yellow | brown |
| Color stability[e] | ++ | ++ | + | + | + | + | + | +/− | ++ | ++ | ++ |
| Smell of the solution[f] | + | + | + | +/− | ++ | ++ | + | +/− | + | + | + |
| Taste of the solution[g] | +/− | +/− | +/− | − | + | + | +/− | − | + | + | + |
| Salt content of the solution[h] | + | + | + | + | +/− | + | + | +/− | + | + | + |
| Glycoalkaloid content[i] | + | − | − | + | + | +/− | +/− | +/− | + | + | + |

-continued

| | Method | | | | | | | | | | |
|---|---|---|---|---|---|---|---|---|---|---|---|
| | 1 Amersham patatin[1] | 2 Amersham PI[2] | 3 Amersham total[3] | 4 Amberlite total[4] | 5 Heat coag. total[5] | 6 Acid coag. patatin[6] | 7 Acid coag. PI[7] | 8 UF total[8] | 9 Fastline Patatin[9] | 10 Fastline PI[10] | 11 Fastline Total[11] |
| Glycoalkaloid content after acidic UF[p] | ++ | + | + | + | N.D. | N.D. | N.D. | N.D. | ++ | ++ | ++ |
| Polyphenol content[j] | + | +/− | +/− | − | − | − | − | − | + | + | +/− |
| Separation of patatin - PI[k] | ++ | ++ | N.A. | N.A. | N.A. | + | ++ | N.A. | ++ | ++ | N.A. |
| Foaming properties[l] | ++ | + | + | + | +/− | +/− | +/− | + | ++ | + | + |
| Gelling properties[m] | + | − | − | − | −− | − | −− | +/− | + | − | − |
| Emulsification[n] | + | − | +/− | N.D. | −− | − | −− | +/− | + | − | +/− |

N.D. means not determined.
N.A. means not applicable.

a Solubility of Spray Dried Product

Solubility is defined as the amount of dry weight protein that can be suspended in water. This is expressed as % of protein in the supernatant after centrifugation of the solution. Solubility is measured for a 3% (w/v) protein solution. "+" means good solubility (>85%); "+/−" means moderate solubility (a suspension is formed with a solubility of between 60 and 85%); − ns low solubility (between 25 and 60%); "−−" poor solubility less than 25% dissolves and precipitates). The solubility strongly depends on the type of drying method and the pH of the protein concentrate prior to drying.

b Solubility Stability

Stability of the soluble protein solution is defined as the condition of being stable or resistant to changes for at least 7 days at room temperature. Microbial stable solutions are obtained by removing contaminating micro-organisms by microfiltrating the samples through a 0.22 µm. After solubilising the protein it either precipitates, dissolves or forms a suspension. The stability describes the state of the solution over at least 7 days since solubilising. For example, at day 1 some dry product dissolves and forms a clear solution. If it is still a clear solution after 7 days it is marked "+" for stability. If there is a lot of precipitation visible after 7 days, it gets a "−". Intermediate states would get a "+/−". But if at day 1 a suspension is formed (without precipitation) and this is still the case at day 7, it also gets a "+", because the state of the solution did not change and looks stable. "+" means good stability; "+/−" means moderate stability; "−" means low stability.

c Solubility at pH 5-7

Solubility is expressed as the % of protein in the supernatant after centrifugation of the solution. "+" means good solubility (>85%); "+/" means moderate solubility (a suspension is formed with a solubility of between 60 and 85%); "−" means low solubility (between 25 and 60%); "−−" poor solubility less than 25% dissolves and precipitates). Solubility (as defined in a) for a protein solution of 3% at pH values between 5 and 7.

d Colour of the Solution

Visual appearance of a 3% protein solution at pH 7.0.

e Colour Stability

Stability (as defined in b) of the colour of the protein solution for at least 7 days. If the colour does not change during 7 days, it gets a "+". If it changes dramatically, a "−" is used. Minor colour changes get a "+/−". "+++" means excellent stability; "+" means good stability; "+/−" means moderate stability; "−" means low stability f Odour of the Protein Solution The odour is determined by a trained panel.
"++" no smell; "+" some smell; "+/−" considerable smell; "−" means bad smell g Taste of the Protein Solution The taste is determined by a trained panel
The flavour of the protein solution. "+" means bland taste; "+/−" means some taste; "−" means bad taste.

h Salt Content

The salt content of the protein solution is determined by the conductivity of 1% (w/v) protein solution. At high protein concentrations the conductivity is dominated by the intrinsic conductivity of the proteins. "+" means low salt content and a conductivity<5 mS/cm; "+/−" means moderate salt content and a conductivity>5 and <10 mS/cm; "−" means high salt content and a conductivity>10 mS/cm.

i Glycoalkaloid Content

Total amount of glycoalkaloids in the protein solution is measured by the method described by Walls et al. (2005). "++" means very low TGA (<150 ppm); "+" means low TGA (between 150-400 ppm); "+/−" means intermediate TGA (between 400-1 000 ppm); "−" means high TGA (>1 000 ppm). The HPLC method of Friedman et al. (2003). is used for specific glycoalkaloids.

j Polyphenols are determined using the Folin-Denis method (Official methods of analysis of the AOAC 7$^{th}$ edition 1950). "+" means<10 ppm; "+/−" means between 10 and 100 ppm; "−" means between 100 and 1 000 ppm; means>1 000 ppm. Concentrations in ppm are based on mg per kg dry matter.

k Separation of Patatin-Protease Inhibitor

Separation of patatin from protease inhibitor is successful when less than 10% of a patatin fraction is contaminated with protease inhibitor. Separation of protease inhibitor from patatin is successful when less than 10% of a protease inhibitor fraction is contaminated with patatin. The separation analysis was based on densitometric scanning of the SDS-PAGE. "++" means excellent separation; "+" means good separation; "+/−" means acceptable separation; "−" means bad separation.

l Foaming Properties

Foam formation is measured by whipping a 3% protein solution for 1 mm. "++" means excellent foaming (overrun>400%); "+" means good foaming (overrun between 300-

400%); "+/−" means intermediate foaming (overrun between 200-300%); "−" means bad foaming (overrun<200%).

m Gelling Properties

The ability of a 4% protein solution to form a gel at pH 7.0 at an ionic strength of 20 mM.

n Emulsification

The ability of a 0.55% protein solution to form an emulsion with 10% sunflower oil at pH 5.0 and 125 mM NaCl.

p Ultrafiltration at Acidic Conditions

The eluates described were further concentrated using regenerated cellulose membranes to remove glycoalkaloids and to obtain a dry matter content of more than 14%. Patatin and total protein isolates were concentrated at pH 5.2. Protease inhibitor isolates were concentrated at pH 3.2.

FIG. 1A shows an SDS-PAGE comparison of the following potato protein isolates.

Lane 1 Molecular Weight marker.
Lane 2 Potato fruit juice (diluted raw material potato fruit juice from the potato factory at Ter Apelkanaal (The Netherlands).
Lane 3 Eluted patatin fraction from EBA with Amersham STREAMLINE® Direct CST I adsorbent (method 1).
Lane 4 Eluted protease inhibitor fraction from EBA with Amersham STREAMLINE® Direct CST I adsorbent (method 2).
Lane 5 Eluted total protein content from EBA with Amersham STREAMLINE® Direct CST I adsorbent (method 3).
Lane 6 Total protein content from AMBERLITE®XAD7HP column material (method 4).
Lane 7 Total protein content obtained by heat coagulation (method 5).
Lane 8 Patatin precipitate by acid coagulation (method 6).
Lane 9 Protease inhibitor precipitate by acid/heat coagulation (method 7).
Lane 10 Total protein content obtained by Ultrafiltration (method 8).
Lane 11 Eluted patatin fraction using EBA with Fastline PRO (method 9).
Lane 12 Eluted protease inhibitor fraction using EBA with Fastline PRO (method 10).
Lane 13 Eluted total protein fraction using EBA with Fastline PRO (method 11 diluted).
Lane 14 Potato fruit juice (diluted raw material potato fruit juice from the potato factory at Ter Apelkanaal (Netherlands).
Lane 15 Molecular Weight marker.

Patatin migrates at a molecular weight of 40-41 kDa. Protease inhibitors migrate at molecular weights of 5-22 kDa. Line 3 shows partial degradation products of patatin.

Photos of the following concentrated isolates are shown in FIG. 1B.

Photo 1 Concentrated patatin fraction (pH 6.1) obtained with EBA and Amersham STREAMLINE® Direct CST I adsorbent.
Photo 2 Concentrated protease inhibitor fraction (pH 7.1) obtained with EBA and Amersham STREAMLINE® Direct CST I adsorbent.
Photo 3 Concentrated total protein content fraction (pH 6.5) obtained with EBA and Amersham STREAMLINE® Direct CST I adsorbent.
Photo 4 Concentrated total protein content fraction (pH 6.5) obtained with AMBERLITE® XAD7HP column material.
Photo 5 Total protein content suspension (pH 5.9) obtained by heat coagulation.
Photo 6 Patatin suspension (H 6.0) obtained by acid coagulation.
Photo 7 Protease inhibitor suspension (pH 5.5) obtained by acid coagulation.
Photo 8 Total protein content solution (pH 7.5) obtained by ultrafiltration.

Example 2

Distinct Gelling Properties of Protease Inhibitor and Patatin Isolates

The gel strength N was determined of patatin and protease inhibitor isolate gels that were prepared with different protein content, different pH values and different ionic strengths. The results are shown in the following table.

| Protein content (%) | pH | Ionic strength (mM) | Patatin isolate gel strength | Protease inhibitor gel strength |
|---|---|---|---|---|
| 5.00 | 5.0 | 125 | 0.154 | 0.025 |
| 7.50 | 5.0 | 125 | 5.600 | 0.020 |
| 10.00 | 5.0 | 125 | 1.597 | 0.237 |
| 7.5 | 3.0 | 125 | 0.196 | 0.101 |
| 7.5 | 7.0 | 125 | 1.554 | 0.161 |
| 7.5 | 5.0 | 50 | 0.970 | 0.166 |
| 7.5 | 5.0 | 200 | 0.783 | 0.096 |

Clear differences of gelling and emulsifying properties between patatin and protease inhibitor isolates can be demonstrated in the experiments at various conditions. To our knowledge there are no data available for gelling properties of patatin isolates and protease inhibitor isolates in the prior art.

Patatin isolates gel better and have superior gelling properties in a pH range of 4.8-5.5. The patatin isolate gives a very pronounced strong gel at pH 5.0 near the iso-electric point of the patatins in that isolate. This makes it very suitable for slightly acidified food products such as yoghurts.

Example 3

Protease Inhibitor and Patatin Isolate Emulsion Activity and Stability

The emulsion activity EA and the emulsion stability ES were determined of protease inhibitor and patatin isolate emulsions that were prepared with different protein content, different oil content, different pH values and different ionic strengths. The native potato protein isolates were obtained according to method 9 for patatine isolate and method 10 for protease inhibitor isolate. The results are shown in the following table.

| Protein content (%) | Oil content (%) | pH | Ionic strength (mM) | Patatin isolate | | Protease inhibitor isolate | |
|---|---|---|---|---|---|---|---|
| | | | | EA | ES (%) | EA | ES (%) |
| 0.10 | 25 | 5.0 | 125 | 0.064 | 45 | 0.040 | 68 |
| 0.55 | 25 | 5.0 | 125 | 0.317 | 11 | 0.423 | 2 |
| 1.00 | 25 | 5.0 | 125 | 0.513 | 77 | 0.396 | 30 |
| 0.55 | 10 | 5.0 | 125 | 0.266 | 73 | 0.146 | 55 |
| 0.55 | 40 | 5.0 | 125 | 0.311 | 49 | 0.290 | 43 |
| 0.55 | 25 | 3.0 | 125 | 0.360 | 60 | 0.173 | 63 |
| 0.55 | 25 | 7.0 | 125 | 0.217 | 62 | 0.263 | 35 |
| 0.55 | 25 | 5.0 | 50 | 0.320 | 74 | 0.273 | 47 |
| 0.55 | 25 | 5.0 | 200 | 0.257 | 48 | 0.163 | 51 |

The patatin isolates give a good emulsion and emulsion stability depending on the ionic strength pH and protein content used. The differences between the protease inhibitor isolates and patatin isolates are small. The patatin isolate gives overall a better emulsion stability.

The stability of Patatin isolate based emulsions can be enhanced by charged hydrocolloids specifically carrageenan and alginate. The stability of protease isolate based emulsions can be enhanced by charged hydrocolloids in particular LM pectin.

Example 4

Relative Gel Strength of Patatin Isolate, Protease Inhibitor Isolate, Whey Protein and Egg White Protein The relative gel strength was determined in 20 mM sodium phosphate buffer at pH 7.0. The relative strength was scaled between 0 to 14. A value of 14 corresponds with a gel of 20% egg white protein.

The following high grade proteins were used:
Whey protein WP-Bi—Bipro, a protein isolate using ion exchange (Davisco Foods International, Le Sueur, USA).
Egg protein EP-HG1—High Gelling (HG) 1800 (NIVE Nunspeet Holland Eiproducten, The Netherlands)
$PAT_S$—Patatin isolate (method 9) spray dried at pH 7.0
$PPI_S$—Protease inhibitor isolate (method 10) spray dried at pH 7.0

Figure 2:
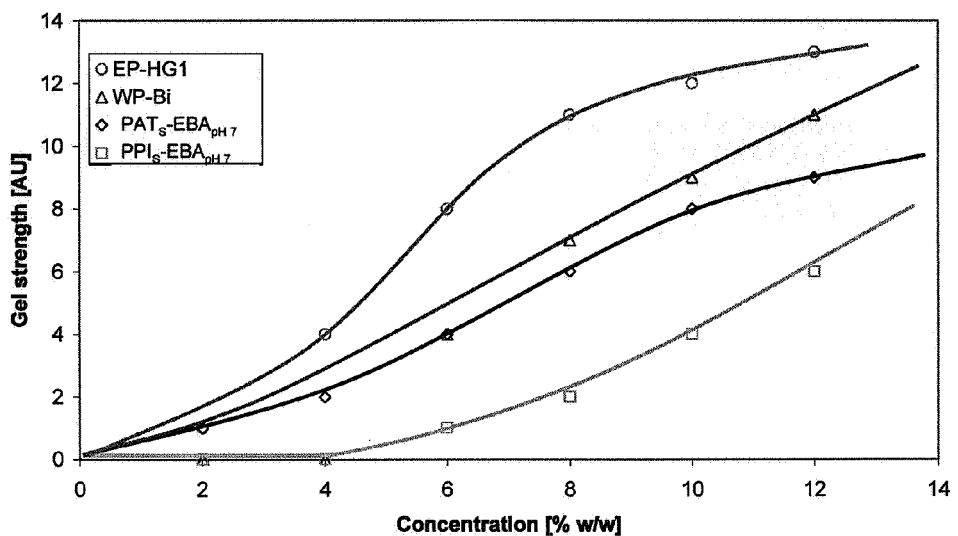
FIG. 2: Relative gel strength of patatin isolate, protease inhibitor (PI) isolate, whey protein, and egg white protein.

The results are shown in FIG. 2. It is clear that patatin isolate gives a similar gel strength to a high grade whey protein Bipro. Under these conditions the protease inhibitor isolate gives a much weaker gel.

Example 5

Figure 3:
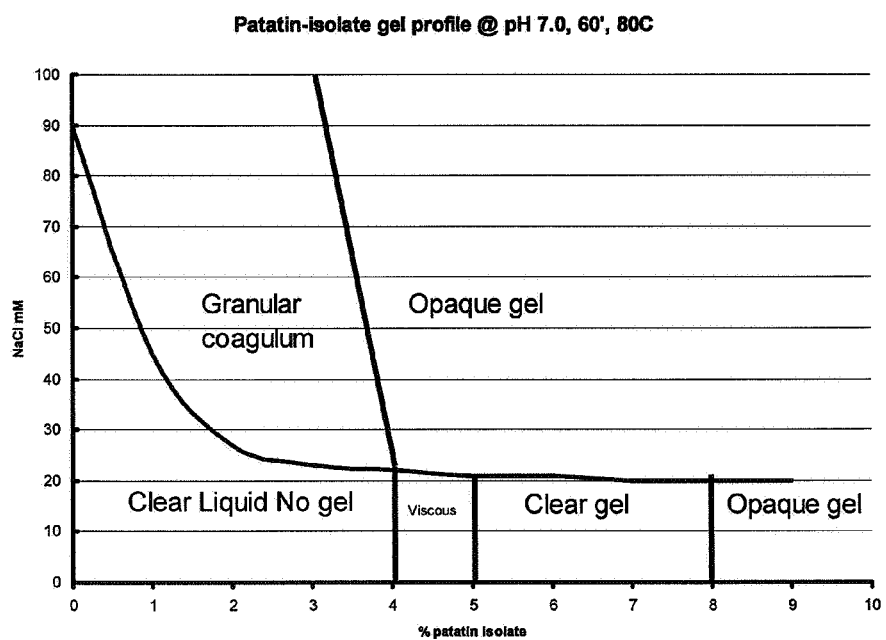
FIG. 3: Appearance of patatin isolate gels as a function of concentration and ionic strength.

Basic Appearance of Patatin Isolate Gels as a Function of Concentration and Ionic Strength Depending on the protein concentration of the patatin fraction and the ionic strength, the protein solution has variable appearance in its gelling properties after a treatment for 1 hour at a temperature of 80° C. at pH 7.0 as shown in FIG. 3. Patatin fraction yields a transparent gel at a unique low concentration of 5-8%. Milk proteins and egg white proteins form gels at concentrations above 8%. The solubility of patatin isolate till turbidity occurs at pH 7.0 is 5%. Patatin isolate has a relatively low gelling concentration threshold of 5% at pH 7.0.

Figure 4:
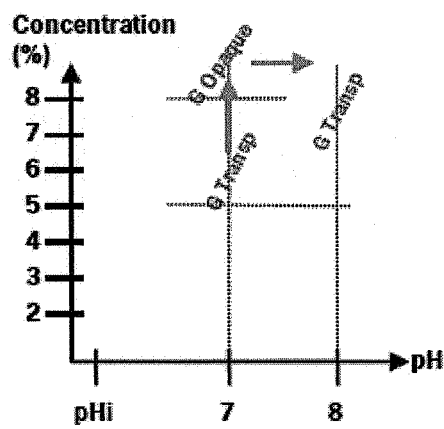
FIG. 4: The effect of pH on the gel transparency of patatin isolate gels.

Patatin isolates form opaque gels at a pH equal or lower than 7.0 and at an ionic strength of more than 25 mM. At concentrations below 4%, or at ionic strengths of less than 25 mM patatin isolates do not yield a gel but a liquid. FIG. 4 shows the effect of the pH on the gel transparency. A clear gel is formed between a pH of 7.0 and 8.0 and at a patatin fraction concentration of 5-8%. The concentration at which clear gels are formed can be controlled by adding small amounts of charged surfactants in a molar ratio of 0.8-3.0. A 1 to 1 molar ratio of patatin fraction: sodium dodecyl sulphate gives a clear gel at 10% vs. an opaque gel at 10% without sodium dodecyl sulphate.

Example 6

The Application of the Potato Isolates in Light Bakery Products Such as Meringues Meringues consist of sugar and protein isolates and are representative of bakery foam products. Isolates of patatin, protease inhibitor and total protein were compared with egg albumin. The potato protein isolates were prepared using isolation method 9, 10 and 11. The chromatography was performed at semi-tech 35 liter scale. All samples were white powders with good solubility and contained more than 90% of protein based in nitrogen content times 6.25 and a glycoalkaloid level of less than 150 ppm.

The mixture mentioned in the recipe was stirred with a Hobart mixer. The overrun was determined as the volume of the total mixture foam before and after stirring. The viscosity was determined with a Brookfield viscometer with a spindle S 93. The texture was analysed with a Stevens LFRA texture analyser. Organoleptic testing was done with the finished baked product.

|  | Recipe I (%) | Recipe II (%) |
|---|---|---|
| Egg albumin protein concentrate |  | 39.9 |
| Potato protein isolate* powder | 4.0 | — |
| Water | 35.9 | — |
| Salt | 0.4 | 0.4 |
| Sugar (1) | 19.9 | 19.9 |
| Sugar (2) | 39.8 | 39.8 |
| Total | 100 | 100 |

*= patatin, protease inhibitor or total protein isolate powder

For the preparation of the meringues, 150 g of egg albumin protein, or a solution of 10% potato protein isolate and 90% water, and 75 g of sugar were whipped up and baked as follows. All batters contained effectively 4% protein.

Water in bowl (20° C.); the powder is added to the water and mixed gently.
Mix vigorously and slowly add the sugar (1), then slowly add sugar (2).
Bake at 130° C. for 45 min, dry for 2 hours at 85° C. in a stove.

The meringues were tested organoleptically after baking. The results are given in the table below.

| Whipping time (min) | Texture strength (mN) | | | |
|---|---|---|---|---|
|  | Patatin | Protease inhibitor | Total protein | Egg albumin |
| 1 | 52 | 87 | 83 | 28 |
| 2 | 78 | 104 | 79 | 113 |
| 3 | 97 | 91 | 89 | 144 |
| 4 | 71 |  | 81 | 100 |

The best possible texture was obtained after 3 min of whipping. For the protease inhibitor isolate an optimum of texture strength is obtained after 2 minutes.

The very good foaming properties compared with egg albumin can be seen in the table below. Protease inhibitor gives the highest overrun values.

| Powder | Patatin isolate | Protease inhibitor isolate | Total protein isolate | Egg albumin |
|---|---|---|---|---|
| Overrun (%) | 443 | 685 | 522 | 218 |
| Texture (mN) | 123 | 104 | 66 | 136 |
| Viscosity cP | 87 000 | 37 000 | 36 000 | 132 000 |

Patatin, protease inhibitor and total protein isolates give a more than two-fold better overrun than egg albumin. The texture and the viscosity is slightly lower than egg albumin. The patatin isolate is comparable with the egg albumin. This means that the patatin is very suitable for foaming applications. The high overrun values show that the patatin isolate is significant more effective than egg albumin. Protease inhibitor and total protein isolates are less suitable for applications with sugar-rich foam, because they are less stabile with a lower viscosity.

The meringues prepared with protease inhibitor isolate show a very soft and brittle final product. The baked product becomes soft within one hour after baking. The protease inhibitor fraction is therefore not suitable for these types of foamy products. The shorter whipping time however gives advantages in some applications where foams are used quickly with low amounts of shear. Blending of protease inhibitor fraction with other structuring proteins may be considered. Total protein isolate gives a lower performance due to the effects of the protease inhibitor in the isolate. All potato protein isolates show a very bland flavour after baking. Especially patatin results in a crispy meringues structure.

Patatin isolate produces a very good foam and meringues and is a very effective substitute for egg albumin. It has distinct and superior properties compared with total potato protein isolates and protease inhibitor isolates.

Example 7

Solubility

Spray drying at high pH improves the solubility of the patatin isolate. Solubility is expressed as % of protein in the supernatant after centrifugation of the solution. The following table shows the solubility of protein isolates of the invention.

|  | % protein as N × 6.255 | Dissolved at pH 7 (%) | Dissolved at pH 4 (%) |
| --- | --- | --- | --- |
| Patatin isolate spray dried at pH 6 | 89.3 | 73 | 64 |
| Patatin isolate spray dried at pH 7 (method 9) | 95.0 | 92 | 95 |
| Total protein obtained after ultrafiltration at pH 7 and spray dried at pH 7 (method 11) | 69.1 | 73 | N.D. |

The patatin isolate showed a high protein content of 95%. This is higher than the high grade whey and egg white proteins that show a protein content in the range of 81 to at most 92%. The solubility of an adequately dried patatin isolate of 92% is comparable to high grade whey and egg white proteins that show a solubility of 97-100%.

Example 8

Foaming Capacity of Potato Protein Isolates at Several pH Values in Water with Low Ionic Strength Potato protein isolates as described in method 9, 10 and 11 were used. A protein solution is shaken to form a foam layer. The amount of formed foam depends on the protein concentration and on the pH of the solution. 100 ml of protein solution at several concentrations in the range of 0.1%-5.0% (w/v), at pH 3.0, 5.0 and 7.0, were added to a Stedum flask and vigorously shaken for 30 seconds. The foam capacity for each protein was plotted as a function of the protein concentration (in g/l). The results as shown in FIGS. 5-10.

Figure 5:
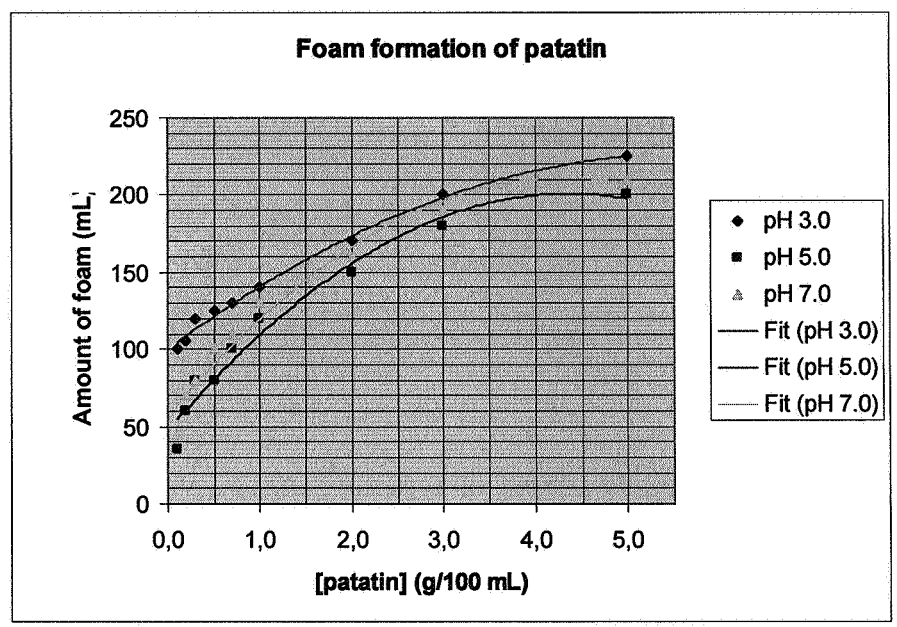
FIG. 5: Foam formation of patatin isolate at several patatin concentrations at pH 3.0, 5.0 and 7.0.
Figure 6:
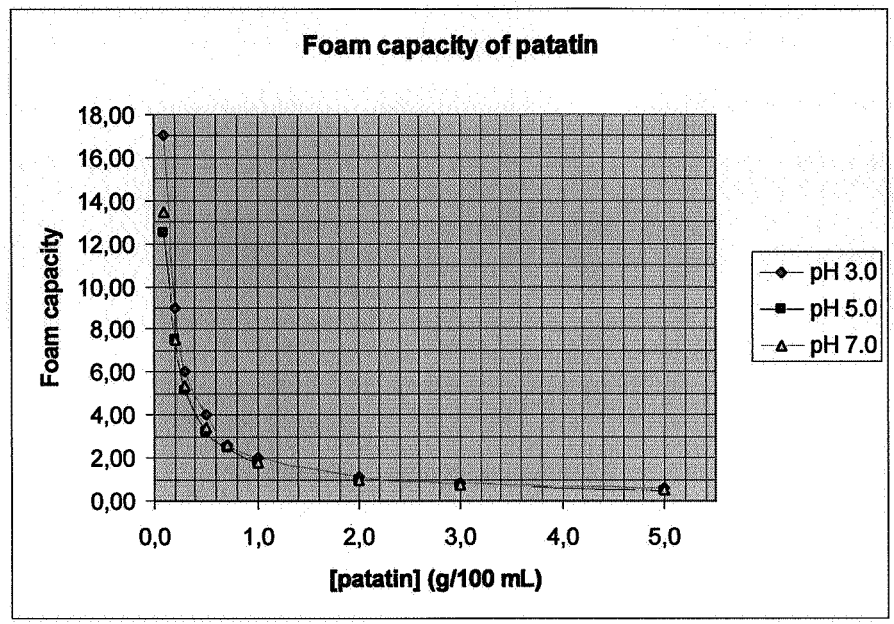
FIG. 6: Foam capacity of patatin isolate as a function of patatin concentration at pH 3.0, 5.0 and 7.0.

The results for patatin are shown in FIGS. 5 and 6. FIG. 5 shows that the largest amounts of foam are formed at a pH of 3.0. This is especially the case at patatin concentrations below 1 g/l. Furthermore, it is clear from FIGS. 5 and 6 that patatin has its best foaming capacity at a pH of 3.0. No significant differences in foaming properties were observed between pH 5.0 and 7.0.

Figure 7:
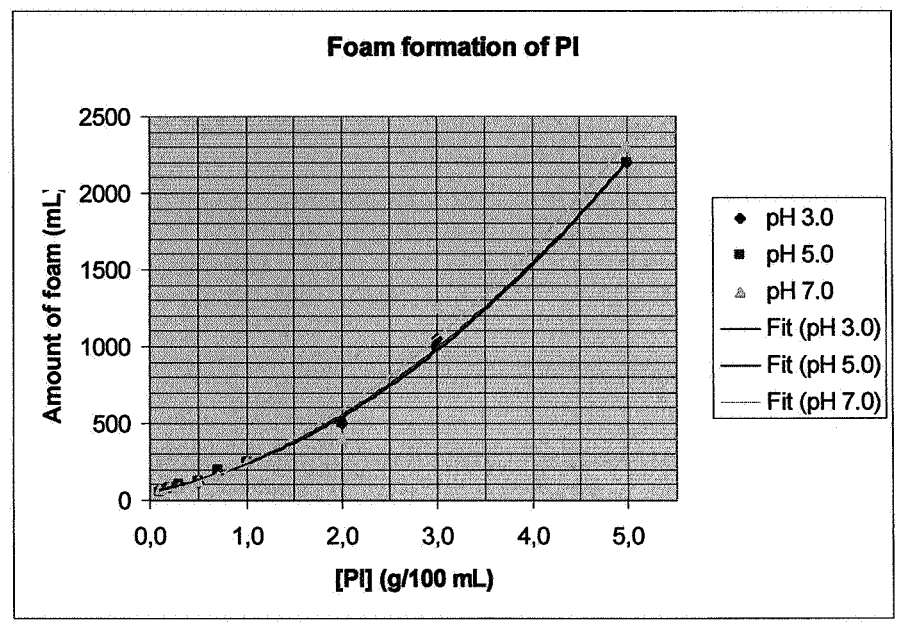
FIG. 7: Foam formation of protease inhibitor isolate at several protease inhibitor concentrations at pH 3.0, 5.0 and 7.0.
Figure 8:
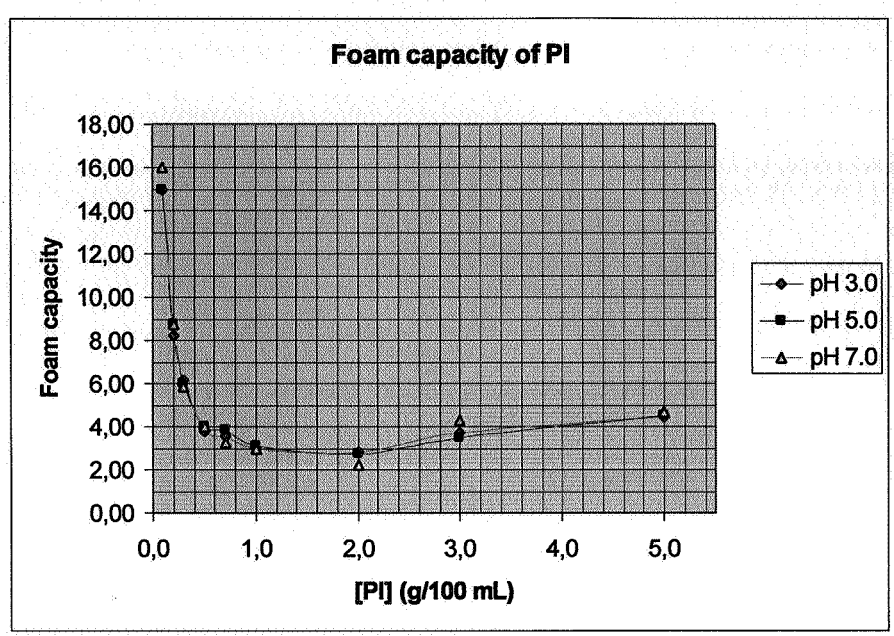
FIG. 8: Foam capacity of protease inhibitor isolate as a function of protease inhibitor concentration at pH 3.0, 5.0 and 7.0.

The results for protease inhibitor are displayed in FIGS. 7 and 8. It seems that the pH did not have any influence on the foam capacity. In contrast to patatin, no decrease of foam formation is observed at higher protein concentrations. In fact, at 5 g/l the formed foam is ten times higher than for patatin. This would indicate that the foaming capacity for protease inhibitors would be ten times higher than for patatin.

Figure 9:
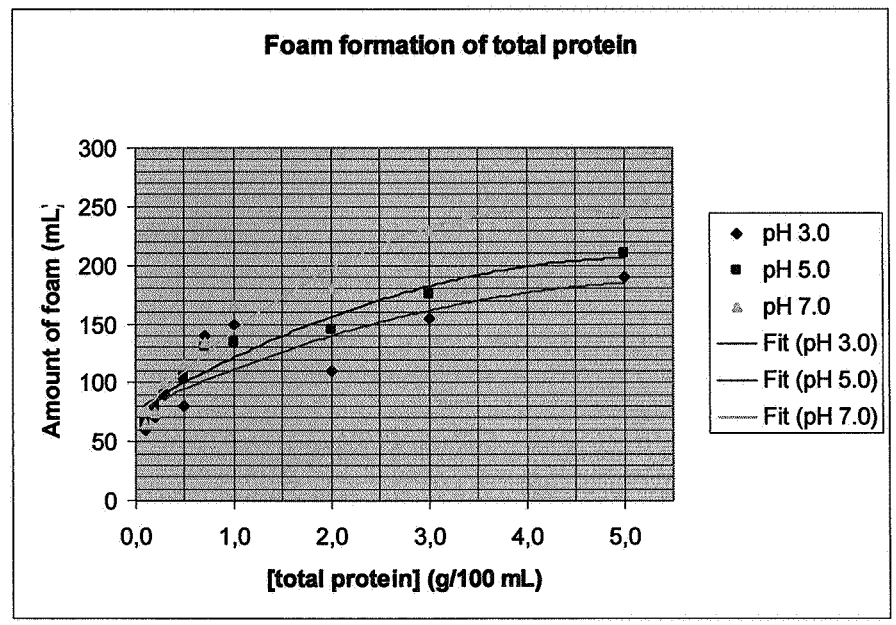
FIG. 9: Foam formation of total protein isolate at several concentrations at pH 3.0, 5.0 and 7.0.
Figure 10:
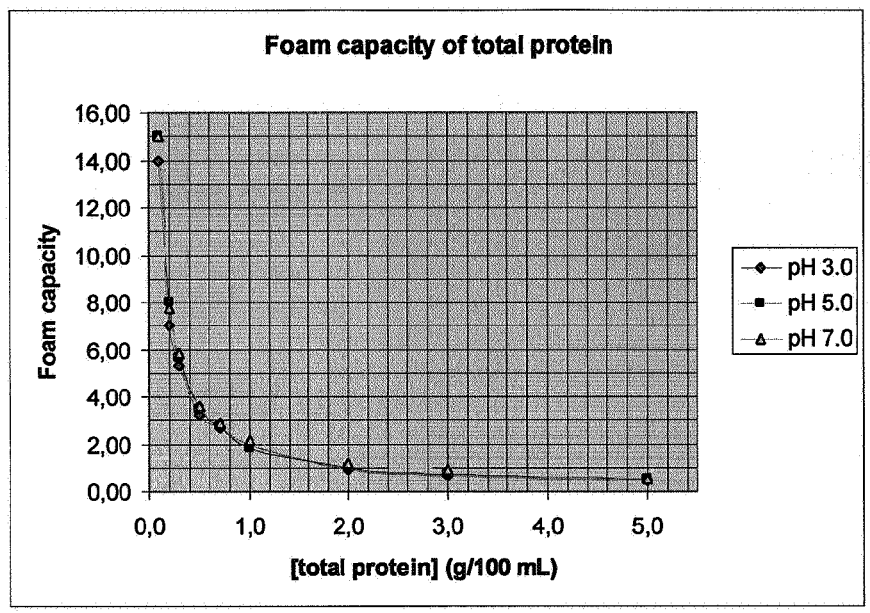
FIG. 10: Foam capacity of total protein isolate as a function of concentration at pH 3.0, 5.0 and 7.0.

The results for total protein isolate are shown in FIGS. 9 and 10.

The protease inhibitor isolates show the highest foaming capacity compared to patatin isolates and total protein isolates. The foaming capacity is not very sensitive to pH. Only the total protein isolate shows a significant pH dependency with an optimum at pH 3.0.

Example 9

Figure 11:
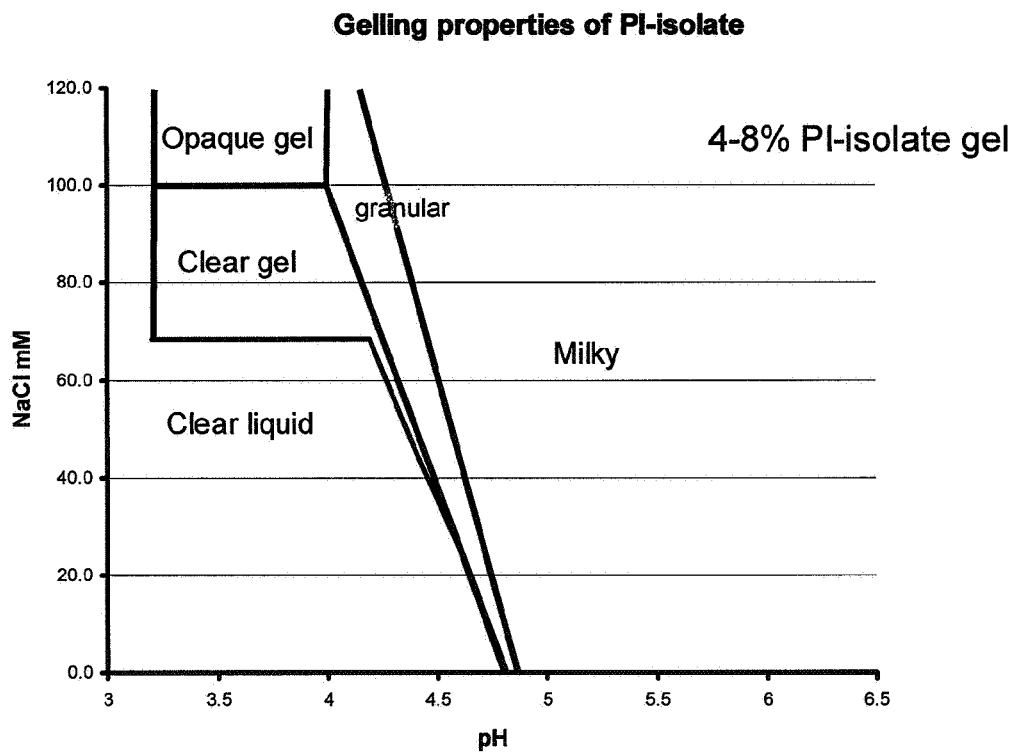
FIG. 11: Appearance of protease inhibitor isolate gels as a function of pH and ionic strength.

Basic Appearance of Protease Inhibitor Isolate Gels as a Function of pH and Ionic Strength The protease inhibitor isolate, the protein solution has variable appearance in its gelling properties depending on the pH and the ionic strength. The appearance after a treatment for 1 hour at a temperature of 80° C. is shown in FIG. 11. The diagram summarises the appearance for a 4-8% protease inhibitor solution. Protease inhibitor isolate yields a transparent gel at a unique low concentration of 4% and a pH. The solubility of protease inhibitor isolate till turbidity occurs at pH 3.5 is >25%. Protease inhibitor isolate has a relatively low gelling concentration threshold of 4% at pH 3-4.4 Protease inhibitor isolates form opaque gels at a pH equal or lower than 4.3 and at an ionic strength of more than 125 mM. Above pH 4.5 protease inhibitor isolates yield stable milky solutions. To our knowledge there are no data available for gelling properties protease inhibitor isolates in the prior art.

The distinct differences in gelling properties of protease inhibitor isolate and patatin isolate is given in the table below. The difference in gelling temperature and pH optimum allow different food and technical applications.

|  | Minimal concentration (%) | pH optimum for gelling | Minimal temperature for gelling at pH 7.0 (° C.) |
| --- | --- | --- | --- |
| Patatin isolate | 4 | 4.8-5.5 | 50-55 |
| Protease inhibitor isolate | 3.5 | 3.2-4.3 | 70-80 |
| Total isolate | 5 | — | 50 |

The low pH optimum for gelling of protease inhibitors isolates makes it suitable for acidic gelled products.

Example 10

Foamed Cream with Milk Cream

A foamed cream is made using an emulsion of fat and potato protein isolate. The emulsion is made using a high pressure homogeniser. Oil coalescencing of high fat emulsions (>10%) is prevented by two passes through the homogeniser. Any undesired hydrolysis of milk fats by the lipase or esterase action of patatin can effectively be removed by heating a 2-5% patatin solution at 70-75C, pH 7.5 for 15-30 minutes.

Figure 12:
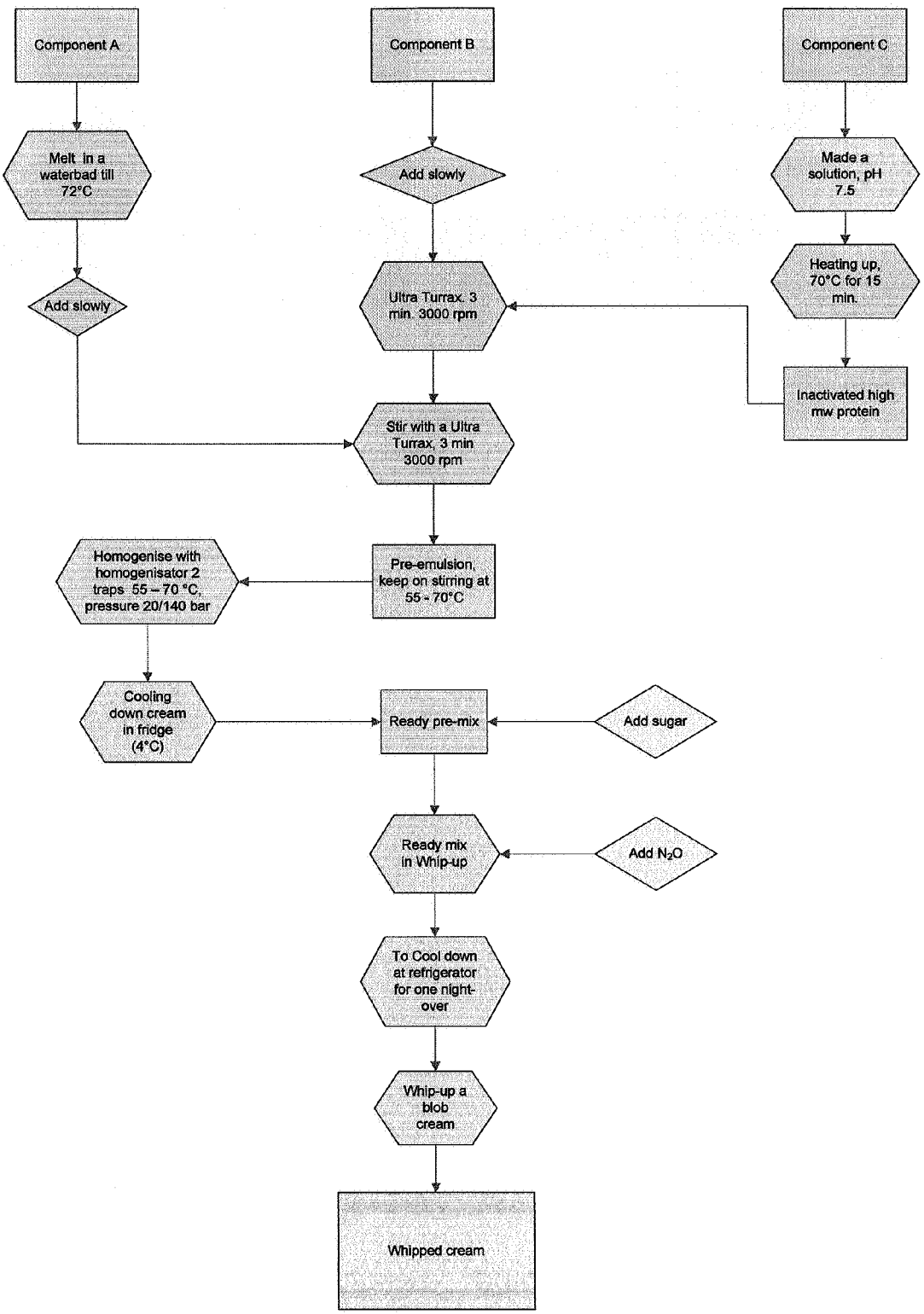
FIG. 12: Flow chart of preparation of foamed emulsion/cream.

Fresh milk cream is blended with patatin isolate. The cream is made according to the scheme shown in FIG. 12. Patatin isolate (a spray dried sample obtained by method 9) is inactivated by heating for 15 minutes at 70° C.). The inactivated, partly gelled, patatin is blended through the cream. The homogeneous emulsion is put in a Dessert whip can with a N$_2$O filling (1.5 bar). The whip can is stored for 12 hours at 5 C. After shaking the whipped cream is released. The resulting volume is measured in a measuring cylinder of 250 ml. The overrun is measured. The foam strength is measured after 5, 15 and 30 minutes with a Lifra-texture analyser (speed 2.0 mm/sec, distance 40 mm). In these series the viscosity is too high to release the cream properly. 15% water is added to reduce the viscosity to acceptable levels while maintaining the fat content to at least 27%. The results are shown in the tables below.

| Run | Cream | Patatin isolate | Water |
|---|---|---|---|
| 1 | 100% | | |
| 2 | 84% | 0.5% | 15.5% |
| 3 | 84% | 1% | 15% |
| 4 | 84% | 2.5% | 13.5% |
| 5 | 84% | 0% | 15% |

| | Overrun | Foam strength stability (load g) | | |
|---|---|---|---|---|
| Run | (%) | After 5 min | After 15 min | After 30 min |
| 1 | 180 | 86 | 68 | 57 |
| 2 | 160 | 25 | 28 | 25 |
| 3 | 180 | 40 | 36 | 34 |
| 4 | 80 | 50 | 48 | 47 |

Run 1: The reference shows an overrun of 180%. This cream contains 2.5% milk protein. A fine structure is observed microscopically. However, the stability of the foam is poor.
Run 2: 0.5% patatin isolate in cream results in a lower overrun than the reference. However, microscopic examination showed a very fine structure. The strength is lower as well.
Run 3: 1% patatin isolate gives a good holding capacity of gas. The structure is a slightly more coarse than the reference, run 1, with a more yellow appearance.
Run 4: 2.5% patatin isolate results in a system which is too viscous to allow good expansion and gas capture. It gives a coarse structure. A reduction of viscosity is needed by lower protein dosing.

These results show that a stable a good foamed cream can be obtained using patatin isolate added to cream, particularly when added in a dosage between 1 and 2.5%. Low amount of syneresis is observed compared with the reference cream.

Example 11

Preparing Foamed Emulsions with Butter Fat Using Patatin Isolates

Extremely stable foamed creams can be made using an emulsion of fat and potato protein isolates. The emulsion is whipped or foamed by using a can with a N$_2$O filling (1.5 bar). The cream obtained using a balanced recipe with fat, a suitable amount of hydrocolloid, has a fine structure, is stable with no to low amount of syneresis. The maximal performance of the patatin or protease inhibitor can be obtained by using fat not cream. Lower amounts of stabilisator, kappa-carrageenenan can be applied. The recipes studied are shown below; they were prepared following the scheme shown in FIG. 12.

Patatin isolates are prepared according to method 9.

| | Sample | | |
|---|---|---|---|
| | 1 % | 2 | 3 |
| Oil phase: Component A | | | |
| Butterfat | 30 | 18 | 30 |
| Water phase: Component B | | | |
| Stabilisator for whipping cream** | 0.04 | 0.04 | 0.01 |
| E472 b esters of mono- and diglycerides | 0.3 | 0.3 | 0.3 |
| Component C | | | |
| Patatin isolate | 1.0 | 2.0 | 1.0 |
| Water | 58.7 | 69.7 | 58.7 |
| After production | | | |
| Sugar | 10 | 10 | 10 |

**Stabilisator is Kappa-carrageenan

Properties of Foam after Expansion:

| | Overrun | Texture | | | | Start Syneresis after |
|---|---|---|---|---|---|---|
| Sample | (%) | 5 min | 15 min | 30 min | 60 min | (min) |
| 1 | 298 | 140 | 111 | 100 | 99 | >60 |
| 2 | 323 | 76 | 59 | 51 | 50 | 20 |
| 3 | 392 | 96 | 70 | 68 | 65 | 30 |

A stable foamed expanded cream can be made using a patatin based butterfat cream. A high overrun with a late on set of syneresis is observed.

Foam stability and strength can be further optimized by adding specific charged hydrocolloids. Extreme synergistic effects were observed by applying patatin together with carrageenan in a ratio of 1:20 to 1:50 carragenan:patatin. Protease inhibitor effects can be enhanced by applying pectin such as LM pectin to the recipes in ratio 1:10 to 1:40 LM pectin: protease inhibitor.

Oil coalescencing of high fat emulsions (>10%) is prevented by to passes through the homogeniser. Extremely stable emulsions can be obtained with both patatin isolate and protease inhibitor isolates.

Any undesired hydrolysis of fats in particular milk fats by the lipase or esterase action of patatin can effectively be removed by heating a 2-5% patatin solution at 70-75° C. up to 80° C., pH 7.5 for 15-30 minutes before making the emulsion. The partly jellified solution is blended with the oil according the scheme in FIG. 12.

Analysis

Overrun is determined using the formula: Overrun (%)=volume before/volume after×100%

The stability of the foamed whipped emulsion is measured after 5, 15 and 30 minutes.

The foam strength or resistance is measured with a Lifra texture analyzer (speed 2.0 mm/sec, distance 40 mm). The colour, taste and smell are measured on of a blub of expanded whipped cream.

Additional comparison with a commercial whipping cream is given.

Recipe
Oil Phase:

| Component A | % |
|---|---|
| Butter concentrate (82% fat) | 37 |

Water Phase:

| Component B | |
|---|---|
| Stabilisator satiagel AcL` | 0.04 |
| E472 b esters of mono-en diglycerides | 0.3 |
| Water | 10.2 |

| Component C | |
|---|---|
| Patatin or protease inhibitor isolate | 1.0 |
| Salt (NaCl) | 0.2 |
| Water | 39.8 |

After Production

| | |
|---|---|
| Sugar | 10.0 |

The lipase activity of patatin can effectively be inactivated by mild heating or parteurisation. In this case the patatin solution is heated for 30 minutes at 75 C to completely remove activity and to avoid off-flavour formation such as butyric acid after 7 days.

Tests:
Reference: Whipped cream (commercial product Friesland Foods, "lang lekker") containing 4% protein.
Test 1: Recipe whipped cream with 1% patatin isolate prepared according to method 9.
Test 2: Recipe whipped cream with 4% protease inhibitor isolate prepared according to method 10.
Measurements on Foams

| | | Texture [load g] | | |
|---|---|---|---|---|
| Sample | % overrun | 5 min | 15 min | 60 min |
| Reference whipped cream | 180 | 86 | 67 | 49 |
| Test 1 | 200 | 24 | 24 | 24 |
| Test 2 | 272 | 39 | 29 | 23 |

Tests with butterfat (without milk protein) with potato protein isolates show that a stable whipped cream can be prepared with 1% patatin isolate. The stability (load g) of whipped cream is stable for one hour and the overrun is at least as good as aerosol whipped cream based on milk proteins. No syneresis is observed. The strength of the foam can be optimized by applying a patatin to carrageenan ration between 1:20 to 1:50.

The results show that 1% patatin in the recipe gives at a similar overrun and a better stability than 4% milk cream based foams.

Whipped cream can also be prepared with higher concentrations, 4%, protease inhibitor isolate. The stability (load g) of whipped cream is at least as good as aerosol whipped cream; the overrun (%) is higher.

Similar results were obtained with patatin with other fats such as palm kernel oil and coconut oil, as shown below.

| Sample | Stability | Structure | Colour |
|---|---|---|---|
| Butterfat 36% | More solid and buttery than normal whipped cream | Regular | Yellow/white |
| Butterfat 18% | Creamy | Regular | White/yellow |
| Palm kernel oil | Solid | Regular | White |
| Coconut oil | Lobby | Regular | White |

This shows the ability of patatin isolates both emulsify various fats to allow the manufacture of fully vegetable based foamed/whipped creams.

Example 12

Preparing Ice Cream with Patatin Isolates

Patatin isolates obtained according to method 9 can be used to prepare stable emulsions also with higher fat content The following recipes show the application of patatin isolate to make a complete potato based ice cream as a milk protein replacement. The use of vegetable fats such as mentioned in Example 11 will allow the manufacture of a fully vegetable based ice cream Standard ice creams have been prepared by using a table top ice machine.

Emulsion 1:
First a 3.3% patatin protein solution was made. The pH was adjusted to 7.2 with 50% citric acid. The solution was heated for 15 minutes at 80° C. in a water bath to inactivate any lipase activity. A 20% emulsion was made with emulsion 1 (60° C.), butter oil (approx. 60° C.) and 0.01% vanillin with an Ultraturrax.

Emulsion 2:
Emulsion 2 was similar to emulsion 1 only the protein content was decreased from 3.3% to 1.65%.

Emulsion 3:
Emulsion 3 was similar to emulsion 1 only patatin isolate was replaced by 11.9% milk powder (protein content approx. 3.3%).

| Recipe 1 | | 1 | 2 | 3 Reference |
|---|---|---|---|---|
| Emulsion 1 | g | 1600 | | |
| Emulsion 2 | g | | 1600 | |
| Emulsion 3 | g | | | 1600 |
| carrageen-solution. | g | 150 | 150 | 150 |
| Sucrose | g | 200 | 200 | 200 |
| Glucidex | g | 50 | 50 | 50 |

| Recipe 1 | | 1 | 2 | 3 Reference |
|---|---|---|---|---|
| Guar | g | | 4 | 4 |
| Emulsifier | g | | | 4 |
| Total | g | 2000 | 2000 | 2000 |

The samples were aged overnight at 4° C. The samples were aerated with a Hobart mixer at speed 2 for 5 minutes. The aerated mix was applied to an ice cream machine and frozen during 18 minutes.
Results:
Stability
After aging the ice cream mixes had the following appearance:
1. small fat layer, further visually homogeneous
2. slightly inhomogeneous and a small fat layer
3. no visual fat layer, slightly buttermilk like
Particle Size Distribution

| | After production | | After aging of emulsion | | After whipping | |
|---|---|---|---|---|---|---|
| Sample | D[3, 2]* | d(0.5)** | D[3, 2]* | D(0.5)** | D[3, 2]* | d(0.5)** |
| 1 | 9.3 | 16.8 | 9.3 | 16.9 | 8.6 | 16.7 |
| 2 | 10.2 | 19.0 | 10.5 | 20.6 | 10.5 | 19.8 |
| 3 | 8.1 | 14.8 | 8.7 | 16.5 | 12.1 | 29.9 |

The particle size distribution based on d(0.5) and D[3,2] show that the fat droplets of the patatin samples were initially larger and more course than the reference 3. This is mainly due to the use of the Ultraturrax which is not very effective. Trials with a homogenizer show a smaller particle size distribution
Results whipping ice cream mixes: the overrun was determined using the following formula: weight of ice cream mix– weight of same volume frozen ice cream×100%

| Sample | Overrun after whipping | Overrun ice cream |
|---|---|---|
| 1 | 77% | 17% |
| 2 | 96% | 119% |
| 3 | 68% | 78% |

Weight of Frozen Ice Cream
During freezing of ice cream 1 the incorporated air was removed, indicating that no stable foam was created. On the contrary the overrun of ice cream 2 and 3 was increased during ice cream preparation. This shows that lower 1.48% patatin protein concentration a higher overrun than a 3.3% milk protein based ice cream.
Sensory Evaluation
In appearance there was a difference between the whiteness of the ice creams. Ice cream 2 and 3 were whiter than ice cream 1. The whiteness is improved by applying a homogenizer.
Only mixture 2 resulted in a good ice cream using a table top ice machine. For comparison an ice cream was made using milk powder instead of patatin isolate powder. The structure and smoothness and mouth feel were similar to the reference ice cream with milk protein.

In recipe developments it was observed that the omission of the emulsifier, glucidex, in combination with lowering the dosing of the patatin isolate resulted in a good product with an equal or better overrun and structure compared with the reference milk powder based formulation. Patatin isolate levels of 2.5% to 1.48% in the final product gave good quality ice creams. This will reduce the food additives in ice cream formulations.

Example 13

A Soluble Satiety Enhancing Protein for Use in Beverage

Satiety effects have been described for the heat stable protease inhibitor fraction in potato, generally described as PI-2 or its break down product as disclosed by Kemin in WO2006/096632. The residual PI-2 activity is characterized by its chymotrypsin inhibiting activity. The undesired trypsin inhibiting activity is mainly related to the heat labile protease inhibitors. Here we show that a soluble protease inhibitor isolate can be used as a source of PI-2 and that it can be employed in a carbonated drink such as a light diet cola. The stability and solubility is shown. No PI-2 is being isolated. The whole PI-isolate is used as such and the undesired PI-1 activity is inactivated in situ during processing of the beverage by a heat treatment. No sediment is formed in this treatment. Or the PI isolate is heat treated separately and used as a concentrate together with inactivated PI-1. PI-2 activity is defined as the remaining protease inhibitor activity after a heat treatment of 30 minutes at 80° C. or 70° C.
A heat treated PI-solution pasteurized and unheated was added to light diet cola. As a reference 25 mM phosphate buffer of pH 3.5 was used. The stability of the trypsin- and chymotrypsin-inhibiting activities activity was determined after 4 weeks storage at room temperature.
Materials and Methods
Protease inhibitor powder prepared according to method 10.
Carbonated beverage: Commercial light diet cola pH 3.0
Trypsin was assayed using the chromogenic substrate Succinyl-L-phenylalanine-p-nitroanilide
Chymotrypsin was assayed with the chromogenic substrate: Succinyl-L-phenylalanine-p-nitroanilide
25 mM phosphate buffer pH 3.5
A description of the samples studied can be found in the following table.

| # | Description | Storage conditions and time |
|---|---|---|
| 1 | 0.5% PI (from 2% RT) in 25 mM phosphate buffer pH 3.5 | 4 wks, 2-8° C. |
| 2 | 0.5% PI (from 2% RT) in light diet cola | 4 wks, 2-8° C. |
| 3 | 0.5% PI (from 2% 70° C., 30') in 25 mM phosphate buffer pH 3.5 | 4 wks, 2-8° C. |
| 4 | 0.5% PI (from 2% 70° C., 30') in light diet cola | 4 wks, 2-8° C. |
| 5 | 0.5% PI (from 2% RT) in 25 mM phosphate buffer pH 3.5 | Directly measured after preparation |
| 6 | 0.5% PI (from 2% RT) in light diet cola | Directly measured after preparation |
| 7 | 0.5% PI (from 2% 70° C., 30') in 25 mM phosphate buffer pH 3.5 | Directly measured after preparation |
| 8 | 0.5% PI (from 2% 70° C., 30') in light diet cola | Directly measured after preparation |

The 2% protease inhibitor isolate solution in demineralised water was divided into two pools of 50 ml. One of these pools was kept at ambient temperature while the other was heated in a water bath at 70° C. for 30 minutes. Both of these pools were again divided into two separate fractions each, creating 4 fractions with a final volume of 25 ml each. These fractions were added to either 75 ml of light diet cola or 75 ml of 25 mM phosphate buffer of pH 3.5, creating 100 ml solutions of heated protease inhibitor isolate in light diet cola, heated protease inhibitor isolate in phosphate buffer, room-temperature protease inhibitor isolate in light diet cola and room-temperature protease inhibitor isolate in phosphate buffer. All four of these solutions were stored at 40° C. for a period of 29 days. After this period, 4 new solutions were made according to the procedure outlined above. These new solutions and the old ones were assayed for trypsin inhibitor activity and chymotrypsin inhibitor activity.

Figure 13:
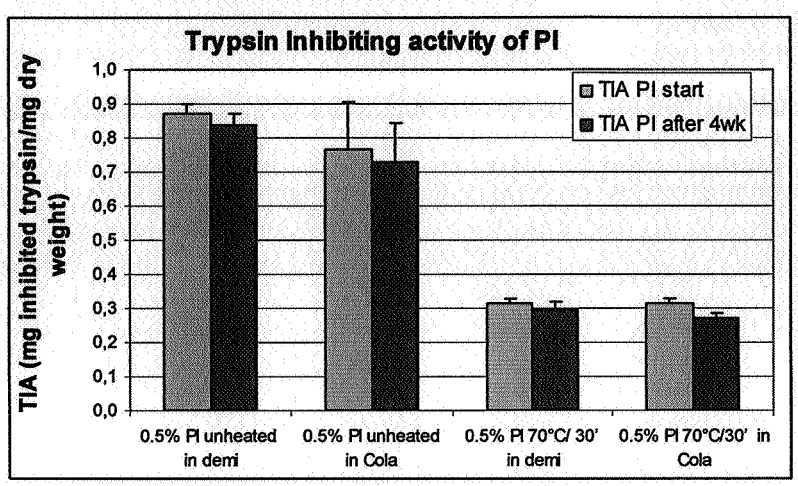
FIG. 13: Trypsin inhibiting activity of PI
Figure 14:
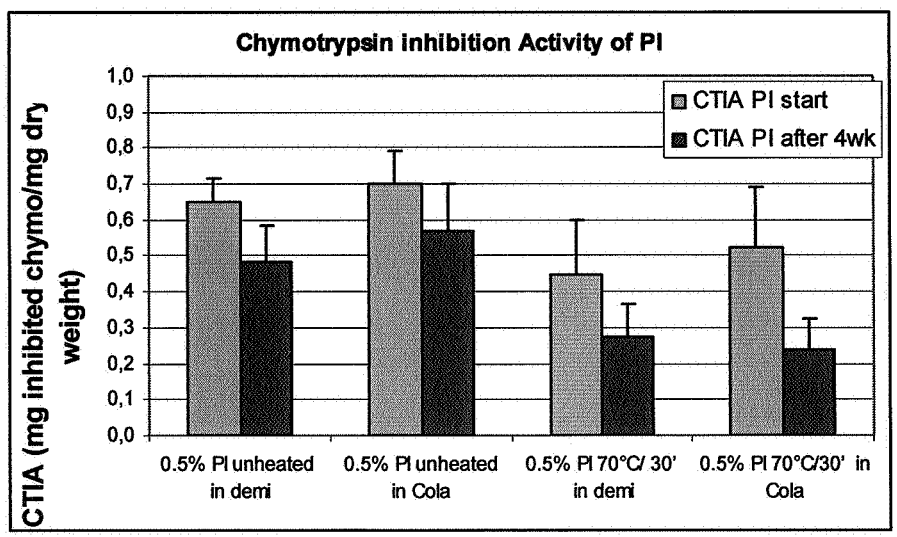
FIG. 14: Chymotrypsin inhibiting activity of PI

The Trypsin- and chymotrypsin inhibiting activities were measured according procedures described by Hirschberg, H. J. H. B. et al. 2001, European Journal of Biochemistry (268) 5037-5044 and Pots, A. M. et al. 1998, European Journal of Biochemistry (252) 66-72. The measured values are shown in the table below and in FIGS. 13 and 14. They are given in TIA which is Trypsin inhibiting activity (mg trypsin inhibited/mg dry weight) and in CT IA (mg chymotrypsin inhibited/mg dry weight).

| # | TIA (mg inhibited Trypsin/mg dry weight protease inhibitor isolate) | Stdev | CT IA (mg inhibited Chymotrypsin/ mg dry weight protease inhibitor isolate) | Stdev |
|---|---|---|---|---|
| 1 | 0.84 | 0.03 | 0.48 | 0.1 |
| 2 | 0.73 | 0.11 | 0.57 | 0.13 |
| 3 | 0.30 | 0.02 | 0.28 | 0.09 |
| 4 | 0.27 | 0.02 | 0.24 | 0.09 |
| 5 | 0.87 | 0.03 | 0.65 | 0.07 |
| 6 | 0.77 | 0.14 | 0.70 | 0.09 |
| 7 | 0.32 | 0.01 | 0.45 | 0.15 |
| 8 | 0.31 | 0.01 | 0.52 | 0.17 |

Under these conditions pasteurisation (70° C. for 30 minutes) of a 2% protease inhibitor isolate solution gives about 60% reduction in trypsin inhibiting activity and about a 50% reduction in chymotrypsin inhibiting activity. All the solutions yielded a clear solution that remained clear.

After 4 weeks the trypsin inhibiting activity in the samples was stable, no sedimentation in the light diet cola was observed. The taste of light diet cola was not altered by the addition of the protease inhibitor. The samples showed some loss in chymotrypsin inhibiting activity. This loss in the in the pasteurised protease inhibitor isolate samples is moderate and stabilizes after 4 weeks. This corresponds well with other trials that showed good stability of 20% solutions of protease inhibitor isolates at pH 3.0-3.2 with close to 100% stable chymotrypsin inhibitor and trypsin inhibitor activity after storage for more than 4 months at room temperature.

The protease inhibitor isolate can be used in a carbonated light diet cola formulation. The liquid remains clear with a relatively stable PI-2 activity. The active dosing of 0.5% protease inhibitor isolate after pasteurisation and prolonged storage yields an effective PI-2 activity of 0.2-0.28%. The residual PI-2 activity can be used in many applications requiring preferably a clear and soluble satiety enhancing composition. The undesired protease inhibitor activities are inactivated prior or during sterilisation of the final product. Heat inactivated protease inhibitor isolate preparations may be produced by heating an isolate as described in method 10 with a relatively low salt content (with conductivity of <3 mS/cm), for 30 at 80° C. or up to 20 minutes at 121° C.

The invention claimed is:

1. Process for obtaining a native potato protein isolate comprising patatin and protease inhibitor, comprising
   i) subjecting potato fruit juice to a flocculation by a divalent metal cation at a pH of 7-9;
   ii) centrifuging the flocculated potato fruit juice, thereby forming a supernatant;
   iii) subjecting the supernatant to expanded bed adsorption chromatography operated at a pH of less than 11 and a temperature of 5-35° C. using an adsorbent capable of binding potato protein, thereby adsorbing native potato protein to the adsorbent; and
   iv) eluting at least one native potato protein isolate from the adsorbent with an eluent.

2. Process according to claim 1, wherein said total native potato protein isolate has an isoelectric point above 4.8, a molecular weight of more than 4 kDa and a glycoalkaloid concentration of less than 150 ppm.

3. Process according to claim 1, wherein said flocculation is carried out at a pH of 7.0-7.5.

4. Process according to claim 1, wherein said expanded bed adsorption chromatography is operated at a pH of less than 10.

5. Process according to claim 1, wherein the eluent has a pH of 4-12, preferably 5.5-11.0.

6. Process according to claim 1, wherein the adsorbent is a mixed-mode adsorbent.

7. Process according to claim 6, wherein a native potato protein patatin isolate is eluted at a pH of 5.7-8.7 and wherein a native potato protein protease inhibitor isolate is eluted at a pH of 5.8-12.0.

8. Process according to claim 6, wherein a native potato protein patatin isolate is eluted at a pH of 5.8-6.2 and wherein a native potato protein protease inhibitor isolate is eluted at a pH of 6.0-9.5.

9. Process according to claim 7, wherein the native potato protein protease inhibitor isolate is further processed into at least one isolate selected from the group consisting of a protease inhibitor I isolate, a carboxypeptidase inhibitor isolate, a protease inhibitor IIa and IIb isolate, and a protease inhibitor A5 isolate by ion exchange or gel permeation chromatography.

10. Process according to claim 6, wherein the mixed-mode adsorbent is used in selective elution mode.

11. Process according to claim 6, wherein the mixed-mode adsorbent is used in selective adsorption mode.

12. Process according to claim 1, which process is followed by an ultrafiltration, at a pH of less than 6.2 to remove glycoalkaloids.

13. Process according to claim 12, at a pH value to increase the flux.

14. Process according to claim 1, which process is followed by a spray drying or freeze concentrating step.

* * * * *

UNITED STATES PATENT AND TRADEMARK OFFICE
CERTIFICATE OF CORRECTION

PATENT NO. : 8,465,911 B2  Page 1 of 1
APPLICATION NO. : 12/513971
DATED : June 18, 2013
INVENTOR(S) : Giuseppin et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 896 days.

Signed and Sealed this
Eighth Day of September, 2015

Michelle K. Lee
*Director of the United States Patent and Trademark Office*